(12) United States Patent
Stanley et al.

(10) Patent No.: US 8,932,325 B2
(45) Date of Patent: Jan. 13, 2015

(54) DEVICES AND METHODS USEFUL FOR SEALING BODILY OPENINGS

(75) Inventors: Cleon Stanley, Bloomington, IN (US); Ram H. Paul, Jr., Bloomington, IN (US); Dennis Griffin, Englewood, CO (US); Sean Chambers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/303,707

(22) Filed: Nov. 23, 2011

(65) Prior Publication Data

US 2012/0116447 A1    May 10, 2012

Related U.S. Application Data

(63) Continuation-in-part of application No. 13/111,338, filed on May 19, 2011.

(60) Provisional application No. 61/346,229, filed on May 19, 2010, provisional application No. 61/351,805, filed on Jun. 4, 2010.

(51) Int. Cl.
*A61B 17/08* (2006.01)
*A61B 17/00* (2006.01)
(Continued)

(52) U.S. Cl.
CPC ... *A61B 17/0057* (2013.01); *A61B 2017/00641* (2013.01); *A61B 2017/00659* (2013.01); *A61B 2017/00592* (2013.01); *A61B 2017/00597* (2013.01); *A61B 2017/00623* (2013.01); *A61B 2017/00628* (2013.01);
(Continued)

(58) Field of Classification Search
USPC .......................................... 606/213, 215–218
See application file for complete search history.

(56) References Cited

U.S. PATENT DOCUMENTS 4,744,364 A * 5/1988 Kensey .......................... 606/213
5,269,809 A * 12/1993 Hayhurst et al. ............... 606/232
(Continued)

FOREIGN PATENT DOCUMENTS

EP    0534696 A1    3/1993
EP    1169968 A1    1/2002
(Continued)

OTHER PUBLICATIONS

International Search Report and Written Opinion issued in PCT/US2012/066173, dated Mar. 8, 2013.

*Primary Examiner* — Dianne Dornbusch
(74) *Attorney, Agent, or Firm* — Woodard, Emhardt, Moriarty, McNett & Henry LLP

(57) ABSTRACT

Among other things, there are disclosed apparatuses and methods for medically sealing an opening in a vessel or wall. For example, in medical applications, a delivery tube is provided for insertion through a sheath into a vessel (e.g. a blood vessel). A dome-shaped seal fixed to a filament, an absorbent and/or compressible buffer, and a locking member are provided in the delivery tube. The delivery tube is configured so that it can be inserted into the vessel through a sheath. Tension is maintained on the filament to hold the seal against the tube or sheath. The sheath is pulled out, which pulls out the tube at the same time, leaving the seal over the opening in the vessel wall. The locking member compresses the buffer against the outside of the vessel and with the filament holds the seal in place against the inside of a vessel.

26 Claims, 17 Drawing Sheets

(51) Int. Cl.
 *A61B 17/04* (2006.01)
 *A61B 17/06* (2006.01)

(52) U.S. Cl.
 CPC ............... *A61B 2017/00663* (2013.01); *A61B 2017/0496* (2013.01); *A61B 2017/06176* (2013.01); *A61B 2017/00407* (2013.01)
 USPC ............................................... 606/213

(56) References Cited

U.S. PATENT DOCUMENTS

| | | | |
|---|---|---|---|
| 5,312,435 A * | 5/1994 | Nash et al. | 606/213 |
| 5,342,393 A * | 8/1994 | Stack | 606/213 |
| 5,350,399 A * | 9/1994 | Erlebacher et al. | 606/213 |
| 5,411,520 A * | 5/1995 | Nash et al. | 606/213 |
| 5,531,759 A * | 7/1996 | Kensey et al. | 606/213 |
| 5,545,178 A | 8/1996 | Kensey et al. | |
| 5,620,461 A | 4/1997 | Muijs Van De Moer | |
| 5,662,681 A * | 9/1997 | Nash et al. | 606/213 |
| 5,700,277 A * | 12/1997 | Nash et al. | 606/213 |
| 5,800,436 A * | 9/1998 | Lerch | 606/324 |
| 5,916,236 A | 6/1999 | Van de Moer | |
| 6,071,301 A | 6/2000 | Cragg et al. | |
| 6,190,400 B1 * | 2/2001 | Van De Moer et al. | 606/213 |
| 6,425,911 B1 | 7/2002 | Akerfeldt | |
| 6,491,714 B1 * | 12/2002 | Bennett | 606/232 |
| 6,508,828 B1 * | 1/2003 | Akerfeldt et al. | 606/215 |
| 6,596,013 B2 * | 7/2003 | Yang et al. | 606/215 |
| 6,764,500 B1 | 7/2004 | Muijs Van De Moer et al. | |
| 6,860,895 B1 * | 3/2005 | Akerfeldt et al. | 606/215 |
| 6,921,401 B2 * | 7/2005 | Lerch et al. | 606/324 |
| 6,939,363 B2 | 9/2005 | Akerfeldt | |
| 7,048,710 B1 | 5/2006 | Cragg et al. | |
| 7,169,168 B2 | 1/2007 | Muijs Van De Moer et al. | |
| 7,338,514 B2 * | 3/2008 | Wahr et al. | 606/213 |
| 7,597,705 B2 | 10/2009 | Forsberg et al. | |
| 7,621,937 B2 | 11/2009 | Pipenhagen et al. | |
| 7,658,748 B2 * | 2/2010 | Marino et al. | 606/213 |
| 7,717,929 B2 * | 5/2010 | Fallman | 606/158 |
| 7,875,052 B2 * | 1/2011 | Kawaura et al. | 606/213 |
| 7,931,671 B2 * | 4/2011 | Tenerz | 606/213 |
| 8,257,389 B2 * | 9/2012 | Chanduszko et al. | 606/213 |
| 8,480,709 B2 * | 7/2013 | Chanduszko et al. | 606/213 |
| 2005/0085855 A1 | 4/2005 | Forsberg | |
| 2005/0169974 A1 | 8/2005 | Tenerz | |
| 2005/0283187 A1 * | 12/2005 | Longson | 606/213 |
| 2006/0142797 A1 * | 6/2006 | Egnelov | 606/213 |
| 2006/0206146 A1 * | 9/2006 | Tenerz | 606/213 |
| 2007/0123936 A1 * | 5/2007 | Goldin et al. | 606/232 |
| 2007/0198059 A1 * | 8/2007 | Patel et al. | 606/213 |
| 2007/0276433 A1 * | 11/2007 | Huss | 606/213 |
| 2008/0071310 A1 * | 3/2008 | Hoffman et al. | 606/215 |
| 2008/0114395 A1 * | 5/2008 | Mathisen et al. | 606/215 |
| 2008/0287986 A1 | 11/2008 | Thor et al. | |
| 2008/0312684 A1 | 12/2008 | Drasler et al. | |
| 2009/0018574 A1 | 1/2009 | Martin | |
| 2009/0054926 A1 | 2/2009 | Pipenhagen et al. | |
| 2009/0112257 A1 | 4/2009 | Preinitz | |
| 2009/0216267 A1 | 8/2009 | Willard et al. | |
| 2009/0234377 A1 | 9/2009 | Mahlin | |
| 2010/0042144 A1 * | 2/2010 | Bennett | 606/213 |
| 2010/0087854 A1 * | 4/2010 | Stopek et al. | 606/215 |
| 2010/0217308 A1 | 8/2010 | Hansen et al. | |
| 2010/0217309 A1 | 8/2010 | Hansen et al. | |
| 2011/0066181 A1 | 3/2011 | Jenson et al. | |
| 2012/0116447 A1 | 5/2012 | Stanley et al. | |

FOREIGN PATENT DOCUMENTS

| | | |
|---|---|---|
| EP | 1266626 A1 | 12/2002 |
| EP | 1413255 A1 | 4/2004 |
| EP | 1440661 | 7/2004 |
| EP | 2 064 999 A2 | 6/2009 |
| WO | WO 99/33402 | 7/1999 |
| WO | WO 00/078226 | 12/2000 |
| WO | 2005/063133 A1 | 7/2005 |
| WO | WO 2006/075228 | 7/2006 |
| WO | WO 2007/059243 A1 | 5/2007 |
| WO | WO 2011/146729 A2 | 11/2011 |

\* cited by examiner

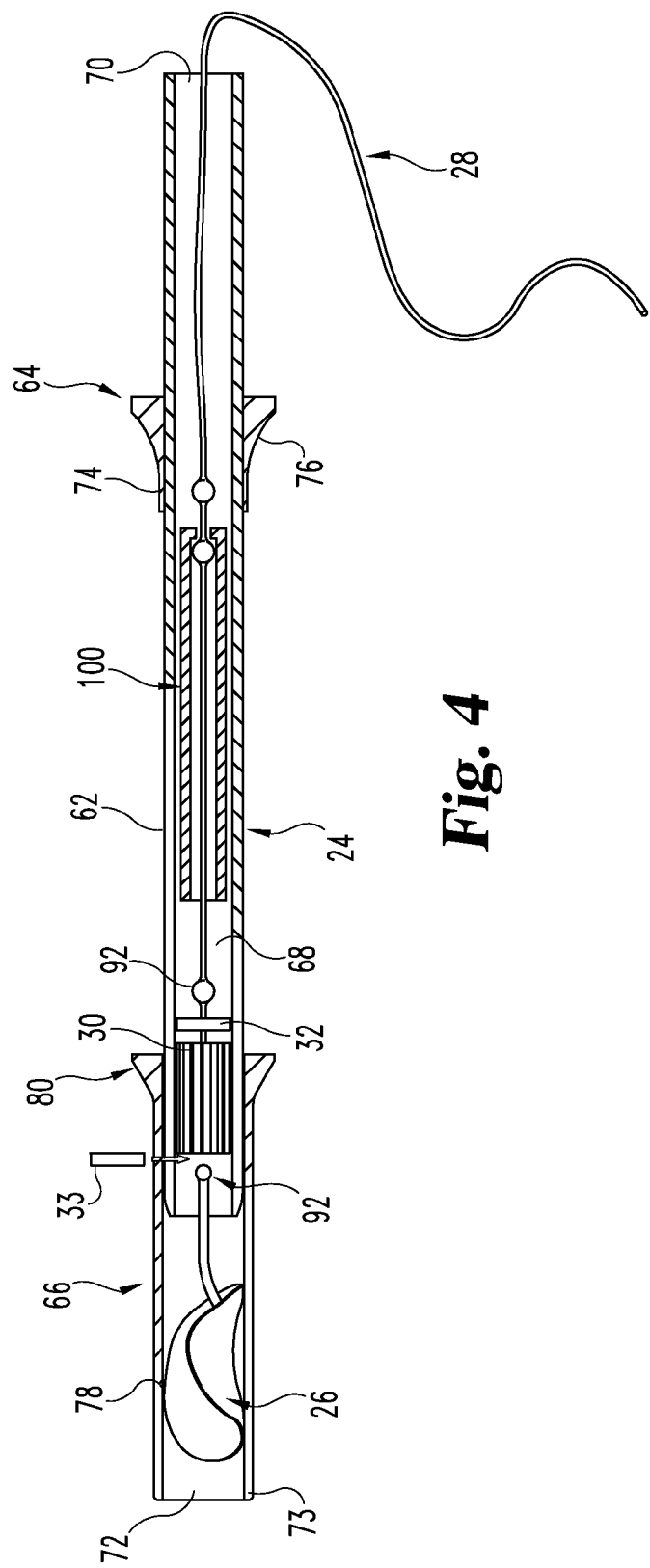

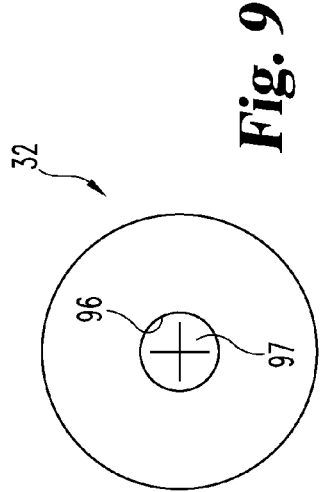
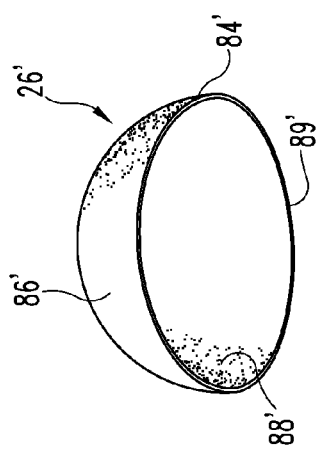
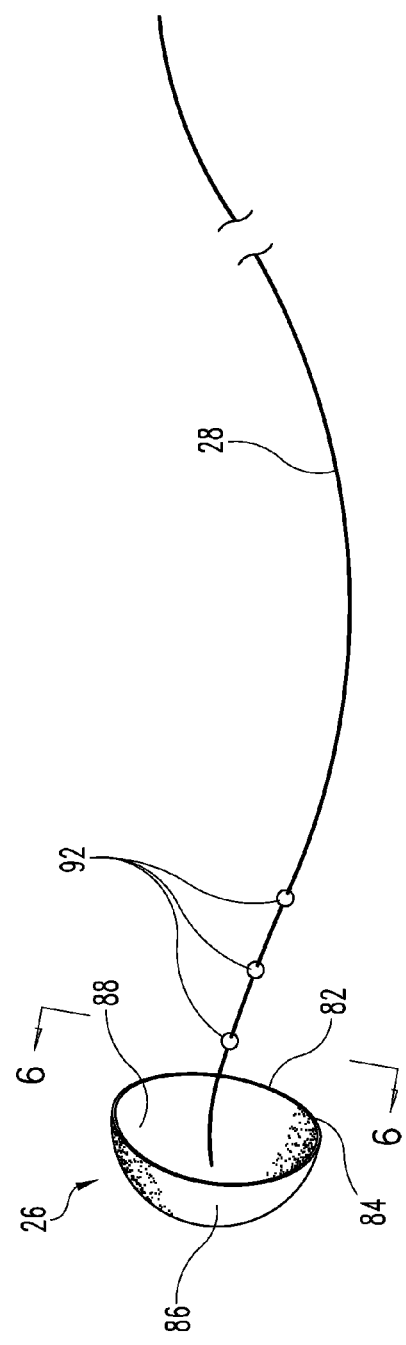

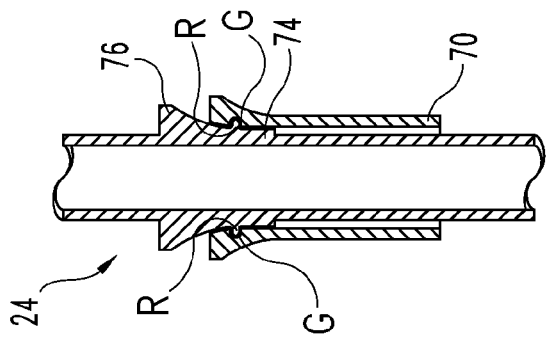
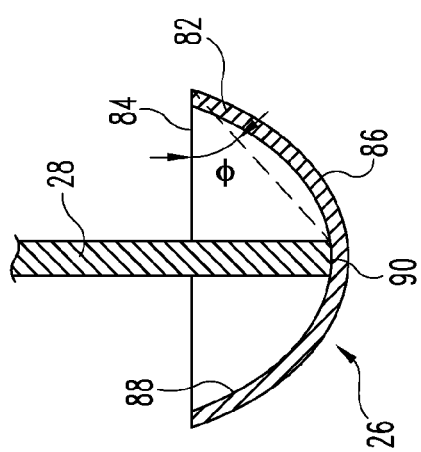
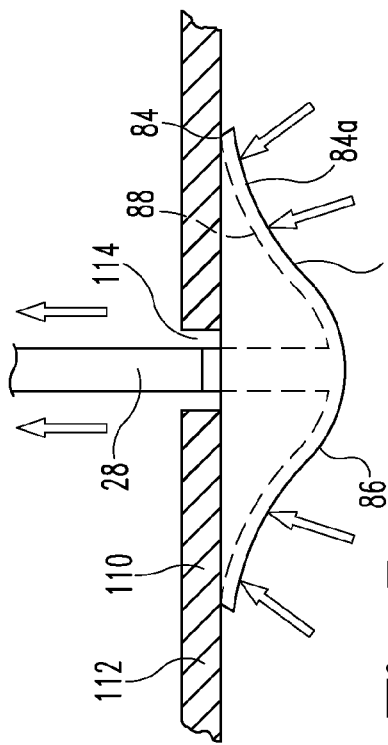

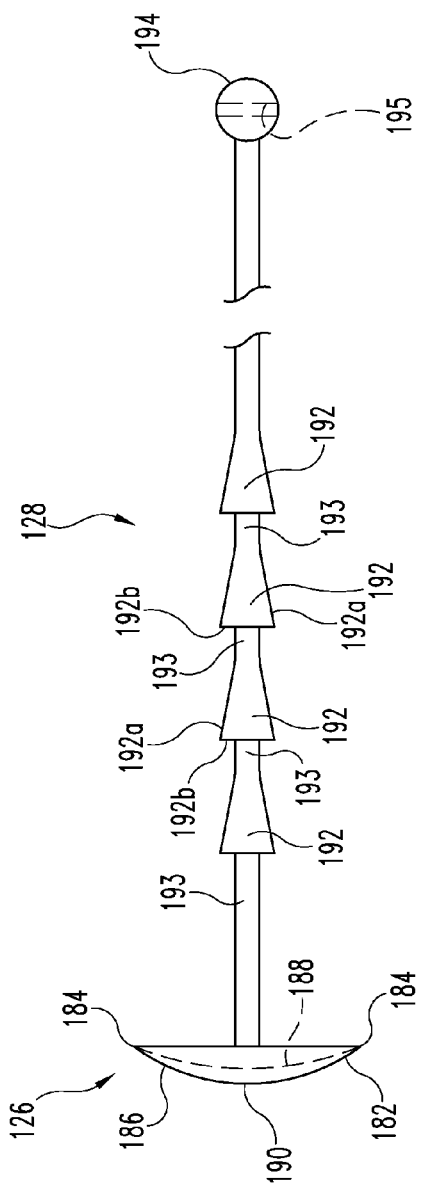
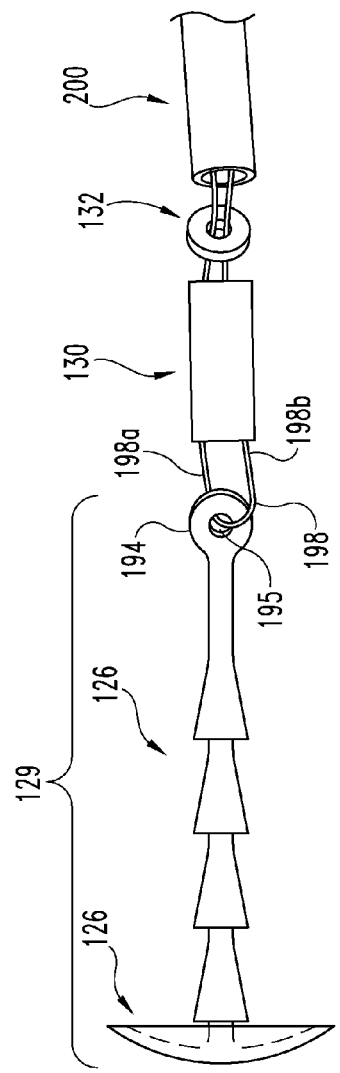
Fig. 8A
Fig. 8B

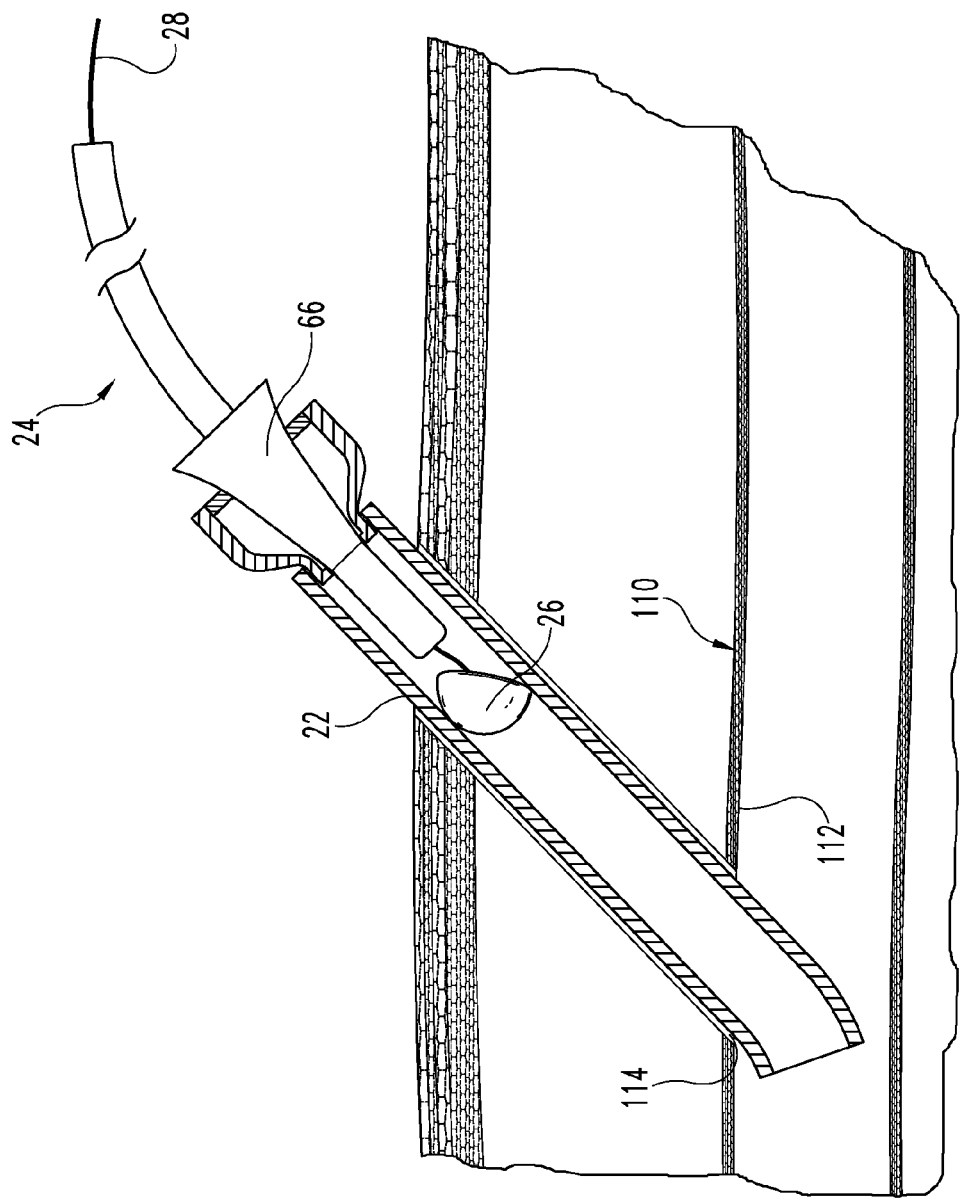

DEVICES AND METHODS USEFUL FOR SEALING BODILY OPENINGS

REFERENCE TO RELATED APPLICATIONS

The present application is a continuation-in-part of U.S. application Ser. No. 13/111,338, filed May 19, 2011, which claims the benefit of U.S. Provisional Patent Application Ser. No. 61/346,229, filed May 19, 2010 entitled "DEVICES AND METHODS USEFUL TO SEALING VESSEL OPENINGS" and U.S. Provisional Patent Application Ser. No. 61/351,805, filed Jun. 4, 2010 entitled "DEVICES AND METHODS USEFUL FOR SEALING BODILY OPENINGS", which are hereby incorporated by reference in their entirety.

BACKGROUND

This disclosure concerns apparatuses and methods useful for sealing an opening in a bodily wall, such as an access opening in the wall of a blood vessel or a fistula. In particular, apparatus and methods are disclosed for closing and allowing healing of an opening in a tissue wall, whether made during a medical procedure (e.g. those in which apparatus or medicaments are introduced into tissue) or naturally occurring (e.g. as a result of malformation or disease).

It has long been known to insert devices into bodily vessels or conduits to provide therapy or for diagnostic purposes. For example, in cardiovascular medicine, it is known to insert catheters, stents and other devices into a patient's vascular system in order to evaluate or treat the patient. In the case of percutaneous transluminal angioplasty (PTA), an opening is made through the patient's skin and into a large or relatively large blood vessel, such as the femoral or iliac arteries, and a balloon is inserted into the vessel and advanced to the location where vessel narrowing has occurred, such as by atherosclerosis. Similar procedures are used to implant stents to maintain flow through blood or other bodily vessels or ducts. In accessing the interior of a blood vessel, the surgeon or medical professional must necessarily breach the integrity of the vessel. A variety of devices (e.g. needles, guidewires, cannulae) are known to open a path into a vessel via a percutaneous opening or other approach. Additional devices or implants can be moved through such devices, or through sleeves or cannulae placed in the opening to keep it open, and into the vessel.

When the procedure is concluded, a cannula or other access device is removed from the vessel, leaving an opening in the vessel. If the arteriotomy is not adequately closed, a subcutaneous hematoma will form. The medical professional must therefore take steps to close the opening in the vessel. In some cases, the opening may be sutured closed, but such action can be very difficult in close quarters, and many vessel-accessing procedures are intended to be minimally-invasive to reduce tissue damage. It is also known to apply constant, film external pressure to the opening in the vessel, particularly if it is a blood vessel, to allow the body's natural coagulation and healing processes to work. In cases in which angioplasty or similar treatment has taken place, however, commonly an anticoagulant has been administered to the patient, making natural closing of the opening in the vessel wall a longer or more difficult process. Maintaining physical pressure on a relatively large blood vessel for a time period sufficient for natural closure also presents at least inconvenience and discomfort to the patient in having to remain still and submit to that pressure, and there is the risk that too much pressure can damage the vessel or tissues that rely on continued flow through it.

Therapies for closing naturally-occurring fistulae or other undesirable bodily openings are also known. Treatments have included closure by suturing or by covering the opening, and by other surgical techniques. Frequently these therapies have required open surgeries with their attendant difficulties.

Devices have been created for inserting closures into a blood vessel or on its exterior that are designed to block the opening and/or soak up fluids that escape the vessel, or are present in the opening through the skin leading to the vessel. Such devices have, however, proven unsatisfactory in many respects, as have therapies for closing naturally-occurring openings in tissue. Needs therefore exist for improved and/or alternative devices and systems for inserting a closure for an opening in tissue that produces a seal without significantly blocking adjacent flow where desired (e.g. through a blood vessel), and fills the opening where that is desirable.

SUMMARY

Among other things, there are disclosed embodiments of parts of a closure system for vascular openings, fistulae, or other bodily openings, which can include a domed seal which when relaxed has a convex exterior surface, an opposite open concave interior surface, and a rim adjacent the convex and concave surfaces. The seal is adapted to contact tissue on one side of an opening (e.g. the interior of a blood vessel or other bodily conduit) at the rim, and in some embodiments at least a central portion of the seal may be non-flush with the tissue when the rim contacts the tissue. A flexible filament is connected to the seal. An absorbent and/or compressible buffer material is along the filament and may be advanceable with respect to the filament. If desired, a retainer disk may be placed between the buffer material and the seal, so that tissue is between the seal and the retainer disk, and the retainer disk is between tissue and buffer material. A compression member is slidably received on the filament, and can have features which cooperate with the filament to fix the position of the two. Illustratively, the filament can have one or more protuberances and the compression member can have an opening which passes with friction over the protuberances, desirably with less force required in a distal direction along the filament than in a proximal direction. A delivery tube having a body portion with a distal end, a proximal end and a lumen extending between and through the ends can also be provided. A proximal boss is fixed with respect to the body and a distal boss is slidable along the body between a position in which a portion of the distal boss is beyond the body's distal end and a position in engagement with the proximal boss. The seal can be folded and located within the distal boss and outside of the body portion of the delivery tube. The filament can extend from the seal through the body portion's lumen, and the buffer and compression member can reside within that lumen with the compression member between the buffer and the proximal end of the body portion.

Embodiments can include a pusher member having a longitudinal passage, with the filament extending through that passage and the pusher member being proximal of the compression member. An external sheath can be provided, for example one having a proximal opening through which the delivery tube can be inserted, so that the tube's distal boss has a portion larger in diameter than that proximal opening. In such cases, insertion of the delivery tube into the sheath results in the sheath contacting the distal boss and holding it stationary as the tube's body portion slides through the distal boss. The distal boss can form a seal with a portion of the sheath. The proximal and distal bosses may each have a respective substantially cylindrical distal portion and an outwardly flared proximal portion, so that part of the proximal boss is adapted to enter within the flared proximal portion of the distal boss, with the proximal boss blocking travel by the distal boss along the body portion of the tube beyond the proximal boss. Some embodiments have a configuration in which one of the bosses has at least one protrusion and the other has at least one complementary indentation, with the protrusion(s) and indentation(s) being positioned so that they meet as an indication that the body portion has traveled a predetermined distance through the distal boss of the tube.

The illustrated embodiments show a buffer with a length substantially greater than its width and surrounding the filament. The buffer can be adapted for compression by the compression member to reduce its length and increase its width to a width greater than that of the body portion of the delivery tube. The buffer may comprise extracellular matrix material, such as small intestinal submucosa. The buffer is a folded or rolled sheet of such material in some embodiments, with a passage allowing the buffer to travel along the filament. In particular embodiments, a buffer is a sheet or ribbon of material (e.g. small intestinal submucosa (SIS) or other extracellular matrix material (ECM)) that is folded accordion style, either initially or on compression in use. A filament as noted above may be threaded or woven into or through such a sheet or ribbon to form a unit, for ease of preparation and control of compression. The buffer can be a foam that expands upon release of compression forces and/or with absorption of fluid to a width greater than the hole to be closed in the wall of the vessel, and the compression member can also be of a diameter greater than the hole to be closed.

Embodiments of a system for use in closing an opening in a vessel wall or other tissue can include a sheath having an insertion portion with a distal end for insertion into the opening in the tissue and a proximal head portion, with the head portion having a proximal opening of a first diameter and a second opening into the insertion portion having a second diameter smaller than the first diameter. A delivery tube has a proximal end, a distal end, and a longitudinal lumen between the ends, and also a first boss slidably attached to the outside of the tube and a second boss fixed with respect to the tube at a position proximal of the first boss. The first boss is slidable between the tube's distal end and the second boss, and it has a distal portion with a diameter less than that of the sheath's proximal opening and forming a close fit with the sheath's second opening. The first boss can have a flared proximal portion, at least part of which is larger than the proximal opening of the sheath's head portion. A seal is folded within the first boss. The seal has a concave internal side and a convex external side, and a filament can be fixed to and extend from the internal side. The filament can have a plurality of spaced stop elements such as protuberances, e.g. in the shape of beads, barbs or frusto-conical sections. A mass of absorbent material can be connected to the filament proximal of the seal, and a retainer disk may be placed along the filament between the seal and the absorbent material. A compression member advancable along the filament and cooperable with the stop elements is proximal of the mass of absorbent material, with the filament extending through the compression member.

Embodiments can also include a flexible seal having a rim adjacent the concave and convex sides, with the seal adapted to engage tissue inside of a vessel or adjacent an opening at the rim. The seal may be adapted to partially or fully flatten against the tissue, so that the rim is urged against the tissue (e.g. a portion of the inside wall of a vessel or conduit). In vascular cases, such an exterior surface presents a profile allowing smooth flow through the vessel. In fistula or other cases, the low profile and/or smooth exterior of the seal presents little or no obstruction with respect to tissues or flow paths adjacent the opening. The seal can include at least one bead along an edge, e.g. in the region of the rim, with the bead(s) configured to engage tissue (e.g. tissue around a fistula, the inner surface tissue of a vessel). The absorbent material may comprise a compressible extracellular matrix material. A pusher member can be included in the delivery tube or placed over the filament at a later time, and used to force the compression member against the buffer to compress the buffer longitudinally, resulting in width expansion and firm engagement with the outside of the vessel. Any or all of the seal, the filament, the buffer and the disk are preferably, but not necessarily, biodegradable.

Methods are also disclosed, such as methods including providing a system as disclosed herein, and inserting a delivery tube from it into a sheath that is within an opening in a patient and through a hole to be closed in tissue. The tube's distal boss engages and is blocked from further insertion by a portion of the sheath. An operator pushes the delivery tube through the sheath so that the distal boss is held stationary and the delivery tube slides through its distal boss, along the sheath and into the vessel. The tube's distal end pushes the seal out of the sheath and through the opening to be sealed (e.g. into a vessel or through a fistula) where the seal expands, such pushing being stopped when the distal and proximal bosses of the tube engage each other. Tension is maintained on the filament during at least a portion of such pushing so that the seal remains adjacent a distal end of the sheath and adjacent the distal end of the delivery tube. The sheath is pulled out of the vessel and the opening in the patient along the filament while maintaining tension on the filament. The seal's rim is pressed against the tissue (e.g. an inner wall of a vessel or rim of a fistula), and the sheath engages the tubes' distal boss to force the tube along the filament with the sheath. A compression member is forced over the filament and beyond at least one stop element of the filament, so that the buffer is compressed against a retainer disk (if present) or against tissue, and interaction of the stop member and the compression member maintain tension on the filament between the compression member and the seal to hold at least the seal's rim in firm engagement with the tissue over the hole. The seal may have a central portion of its exterior surface that remains convex, and a part of that exterior surface that has at least a slight concavity between that central portion and the rim when the seal is engaged against the tissue. The exterior surface of the seal can have a configuration that allows smooth flow or minimal obstruction along it within the vessel or other tissue. Such an exterior surface may absorb pressure from flow or other internal conditions on the central portion that presses the rim against tissue.

Other embodiments include a tissue-opening closure system having a seal device with a relaxed configuration with a domed shape including a convex exterior surface, an opposite open concave interior surface, and a rim adjacent the convex and concave surfaces. The seal is adapted to contact a tissue surface along at least a portion of the concave interior surface. A flexible filament or stem is fixed to the seal device and has a plurality of protuberances fixed thereto and a hole, e.g. at a proximal (non-seal) end. A suture is threaded through the hole and extends away from the seal device, and a compressible buffer is connected to the filament or stem and is slidable with respect to the filament or stem and its protuberances. A locking member having an opening is adapted to slide along the filament or stem and allows the protuberances through its central opening but the protuberances resist travel back through the opening. The locking member is slidable along the filament or stem so as to compress the compressible buffer. In some embodiments, the suture is movable with respect to the stem or filament, and the stem of filament and seal device are monolithic and made of the same bioresorbable material. The buffer may be initially connected to the stem or filament in a position along the suture, so that the buffer is slidable along the suture and then over the stem or filament. In particular embodiments, the buffer is initially in a substantially cylindrical form when positioned along the suture, and is adapted to flatten through moving along the stem or filament and being compressed against tissue. For example, the suture can pass through the buffer in a predetermined manner so that when the buffer flattens it assumes a desired non-cylindrical flattened form. The seal device may be circular, oval, tear-shaped, leaf-shaped and/or shaped of overlapping at least part circular portions. It may include one or more protrusions for engaging tissue extending from the concave interior surface.

Also disclosed are embodiments of devices for closing a hole in a bodily vessel that include a flexible monolithic structure including a domed seal member and a filament connected to the seal member. The seal member is sized and configured for receipt against an interior surface of the vessel to cover the hole, and in a relaxed configuration the seal member has a convex exterior surface, an opposite open concave interior surface, and a rim adjacent the convex and concave surfaces. The filament has an unstressed state in which it has a linear longitudinal axis and is yieldingly resilient, and it extends away from the open concave interior surface without application of force to the filament. Frustoconical protrusions along the filament and an end portion having a hole that is non-parallel to the longitudinal axis of the filament are in some embodiments. The domed seal member is elastically deformable under tension applied through the filament to partially or completely flatten the domed seal member whereupon at least part of the initially concave interior surface is forced against the interior surface of the vessel.

Embodiments in which the monolithic structure is formed of biodegradable materials from the group consisting of polyglycolic acid polymer, polycaprolactone and mixtures thereof are contemplated. In some examples, a suture extends through the hole of the end portion, as where the suture is looped through the hole. A buffer of biodegradeable material can be operatively connected to the filament to be moved along the seal member, and such a buffer may be formed in folds. For instance, a buffer may include a number of sections separated by folds, with the suture extending through a plurality of the sections, and the point at which the suture goes through each of the sections varies from section to section. Such buffer sections may only partially overlap each other in use so that said sections span an area larger than the area of any particular section. The inner concave surface of the seal member can have at least one protrusion raised above the concave surface and positioned laterally to the filament, and such a protrusion may be least one bead, e.g. forming a ring around the filament, or one or more barbs. Such protrusions may be monolithic with and made of the same material as the seal member.

Additional embodiments of the disclosure, as well as features and advantages thereof, will be apparent from the descriptions herein.

BRIEF DESCRIPTION OF THE DRAWINGS

FIG. 4 is a cross-sectional view of the embodiment of a delivery tube as in FIG. 1, taken along the lines 4-4 in FIG. 1 and viewed in the direction of the arrow.

FIG. 5 is a perspective view of embodiments of structure used in the system of FIG. 1.

FIG. 6 is a cross-sectional view of the embodiments shown in FIG. 5, taken along the lines 6-6 in FIG. 5 and viewed in the direction of the arrows.

FIG. 7 is a view of the embodiment shown in FIG. 5 with tension applied to deform it against a vessel wall.

FIG. 8 is a perspective view of another embodiment of a portion of the structure shown in FIG. 5.

FIG. 8A is a side view of another embodiment of a portion of the structure shown in FIG. 5.

FIG. 8B is a side view of the embodiment of FIG. 8A with additional structure.

FIG. 9 is a top view of an embodiment of structure used in the system of FIG. 1.

FIG. 10 is a cross-sectional view of a portion of the embodiment of FIG. 1 in a particular configuration.

FIGS. 11-14 are part-cross-sectional views of the system of FIG. 1 in use in one embodiment.

DETAILED DESCRIPTION

Figure 1:
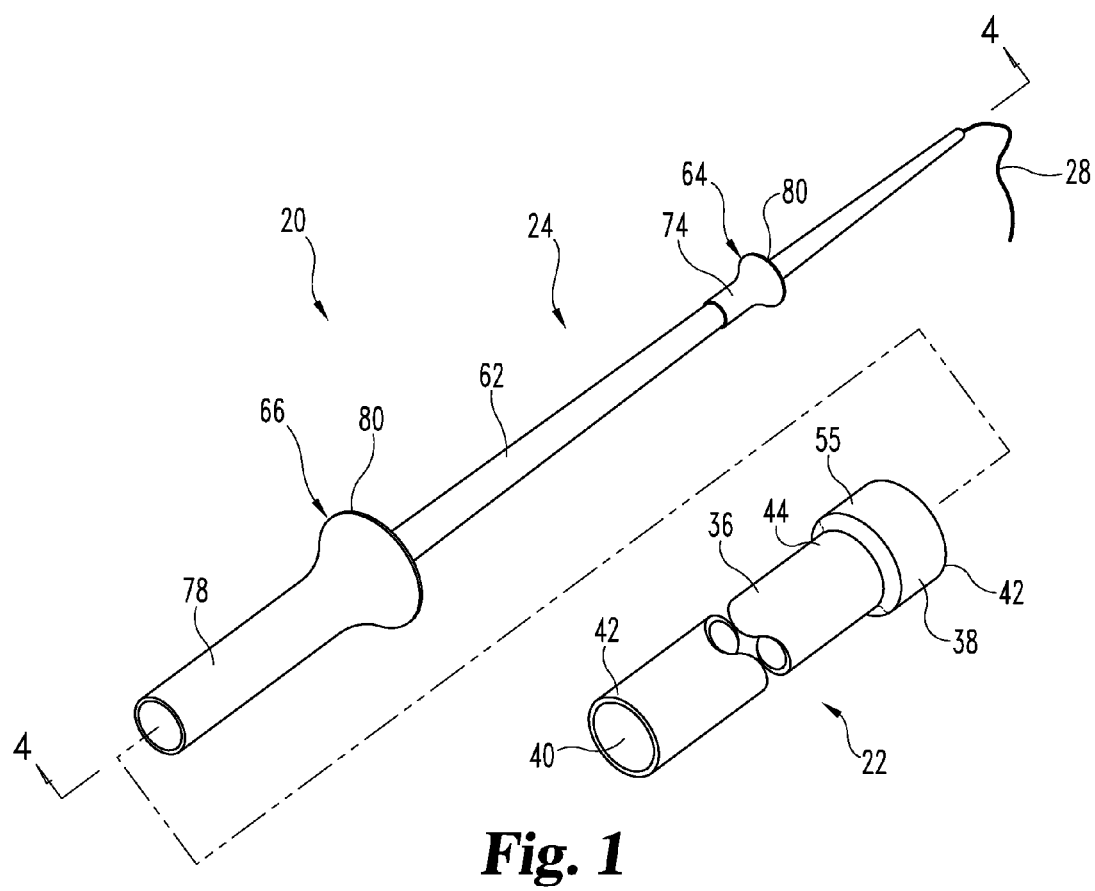
FIG. 1 is a perspective view of embodiments of parts a system for sealing openings in vascular walls.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated devices and methods, and further applications of the principles of the disclosure as illustrated therein are herein contemplated as would normally occur to one skilled in the art to which the disclosure relates.

Referring generally to the drawings, there is shown an embodiment of a system 20 for closing an opening in a wall of a vessel, conduit or other bodily cavity. The description below will focus on use in blood vessels of a human or animal, but it will be understood that the structures disclosed herein have application to a number of other vessels or conduits or bodily cavities. Closure or treatment of undesired openings in a variety of tissues can be performed with structure and methodology as disclosed. Examples of other applications include sealing primary and/or secondary openings of a fistula, with healing or correction (e.g. filling) of the fistula between the openings. Such fistulae may include vesico-vaginal fistulae, which are abnormal passages between the vagina and bladder.

An embodiment of an outer sheath 22 is shown, which may be a part of system 20. This embodiment of system 20 includes an inner delivery tube 24, and repair structure initially inside of tube 24 including a seal 26, a filament 28, an absorbent buffer 30, and a locking or compression member, which is shown as a disk 32 in the illustrated embodiment. An additional retainer disk 33 can be provided in some embodiments. It will be understood that other shapes for the compression member, such as rods, beads or cross-bars, could also be used. In some embodiments, one or more aspects of the repair structure are pre-loaded into tube 24, and tube 24 is pre-loaded into sheath 22, while in other embodiments such loading can take place in preparation for a medical procedure or as the procedure is underway.

Figure 2:
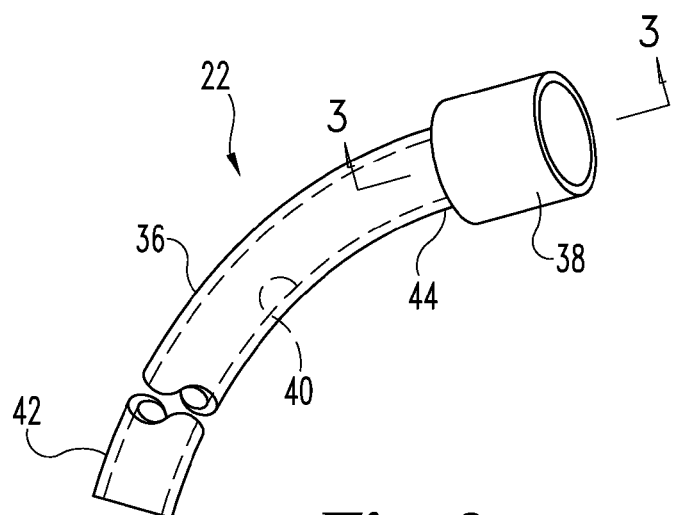
FIG. 2 is a perspective view of an embodiment of a sheath as in FIG. 1.
Figure 3:
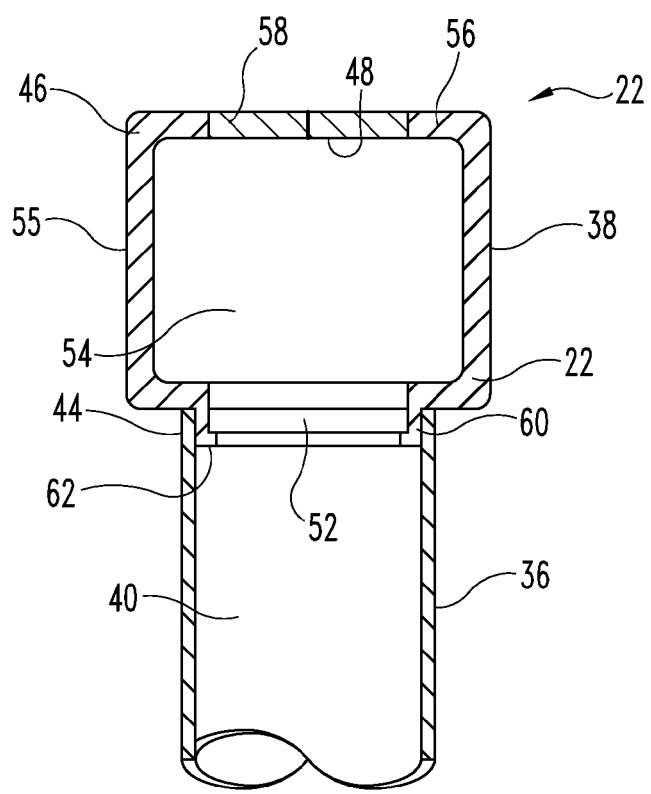
FIG. 3 is a cross-sectional view of the embodiment shown in FIG. 2, taken along the lines 3-3 in FIG. 2 and viewed in the direction of the arrows.

Sheath 22 is shown in one embodiment as including a tubular body portion 36 and a head 38. Body portion 36 is substantially cylindrical in this embodiment and has a lumen 40 of substantially constant inner diameter extending from a distal end 42 to a proximal end 44. Body portion 36 is flexible in this embodiment, capable not only of lateral bending or flexion (e.g. FIG. 2) but also of some radial compression or expansion. Body portion 36 accordingly can be inserted through openings that are not straight, and can also bend into or when entering or within a vessel.

Head portion 38 has a proximal portion 46 with an opening 48 and a distal portion 50 with an opening 52. In the illustrated embodiment opening 48 is larger in diameter than opening 52, and opening 52 is also smaller than the lumen 40 of body portion 36. Connecting and including openings 48 and 52 is an open passage 54 surrounded by a side wall 55. Proximal portion 46 has an inwardly-directed extension 56 in this embodiment, which surrounds or is beyond opening 48 in head portion 38. A sealing flange or member 58 may be placed across or along or included as a part of extension 56, and if included is a flexible member and may have a hole or scoring to allow part of delivery tube 24 through while maintaining or approximating a seal around it. Distal portion 50 includes a longitudinal extension 60 with an inwardly-directed flange 62, through which opening 52 extends. In this embodiment, body portion 36 attaches to head portion 38 by inserting extension 60 of head portion 38 into lumen 40 at proximal end 44 of body portion 36. Extension 60 has a tight fit within lumen 40, to provide a firm connection and seal between head portion 38 and body portion 36. It will be understood that in other embodiments head portion 38 and body portion 36 may be monolithic, e.g. formed together in a mold.

Delivery tube 24 has a main body portion 62, a proximal or upper boss 64 and a slidable distal or lower boss 66. Body 62 is a cylindrical tube in this embodiment, with a constant-diameter lumen 68 extending throughout between a proximal opening 70 and a distal opening 72 at end 73. Upper boss 64 is fixed with respect to body 62, and may be monolithic with body 62 or made separately and fixed to body 62, as by gluing or welding. In the illustrated embodiment, boss 64 has a substantially cylindrical part 74 that flares outward into a widened part 76, to give a shape akin to the bell of a trumpet. Lower boss 66 has a similar shape, with a cylindrical part 78 and a flared part 80, and is slidable between distal opening 72 and upper boss 66. Flared part 80 of lower boss 64 allows cylindrical part 74 of upper boss 66 to enter it (e.g. FIG. 10, 12), and flared part 76 of upper boss 66 engages the flared part 80 of lower boss 64 to stop travel of boss 64 along body portion 60 of delivery tube 24.

Lower boss 64 of delivery tube 24 is sized to be able to be at least partially inserted into head portion 38 of sheath 22. In particular embodiments, cylindrical part 78 of lower boss 64 is smaller in diameter than opening 48 (and extension 56, if present), and in some embodiments has a diameter approximately the same as or slightly larger than that of opening 52 (or flange 60, if present), so that cylindrical part 78 and opening 52 or flange 60 will have a close or sealing fit. Flared portion 80 of lower boss 64 is larger in diameter than opening 48 and/or extension 56. As will be discussed further below, delivery tube is inserted into sheath 22 by first placing boss 64 into head portion 38. Cylindrical part 78 is inserted through head portion 38 until flared portion 80 is stopped by extension 56 or other part of head portion 38. In that relative position, cylindrical part 78 of lower boss 64 extends through head portion 38 of sheath 22, forming a seal with head portion 38 in opening 48 and/or flange 60. With lower boss 64 stably inserted into head portion 38, body portion 60 of delivery tube 24 can be slid through lower boss 64 until upper boss 62 engages lower boss 64. Such sliding movement of body portion 60 permits its distal opening 72 to travel through tubular body portion 36 of sheath 22 and out of its distal end 42. Delivery tube 24 is sized and configured with respect to sheath 22 so that when bosses 64, 66 engage each other, end 73 of body 62 is beyond the distal end 50 of sheath 22.

Figure 5A:
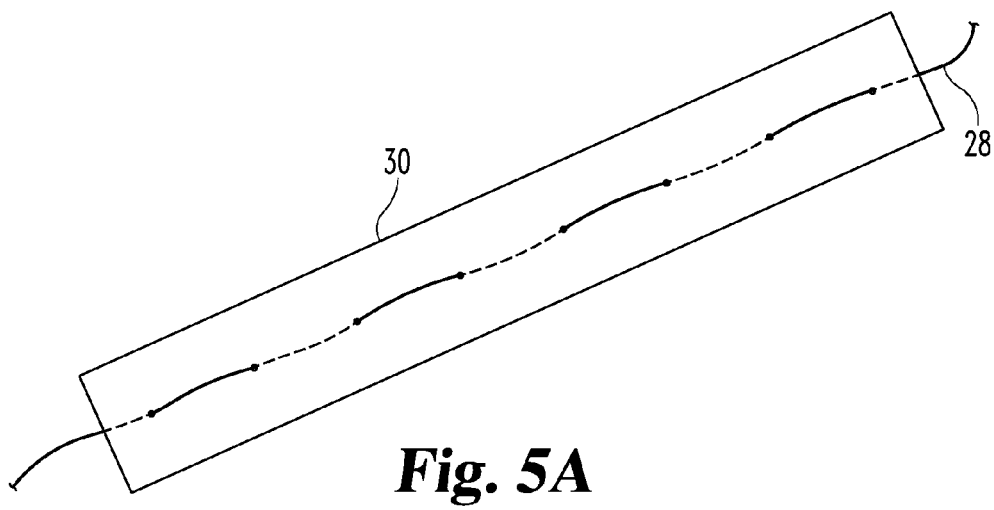
FIGS. 5A-5B are views of embodiments of structure usable in the system of FIG. 1.
Figure 5B:
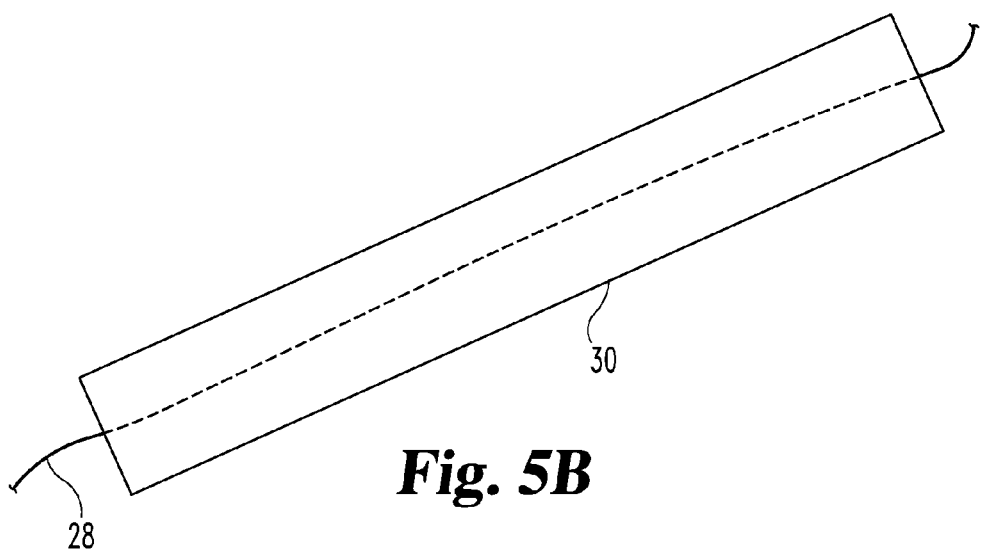
Figure 12:
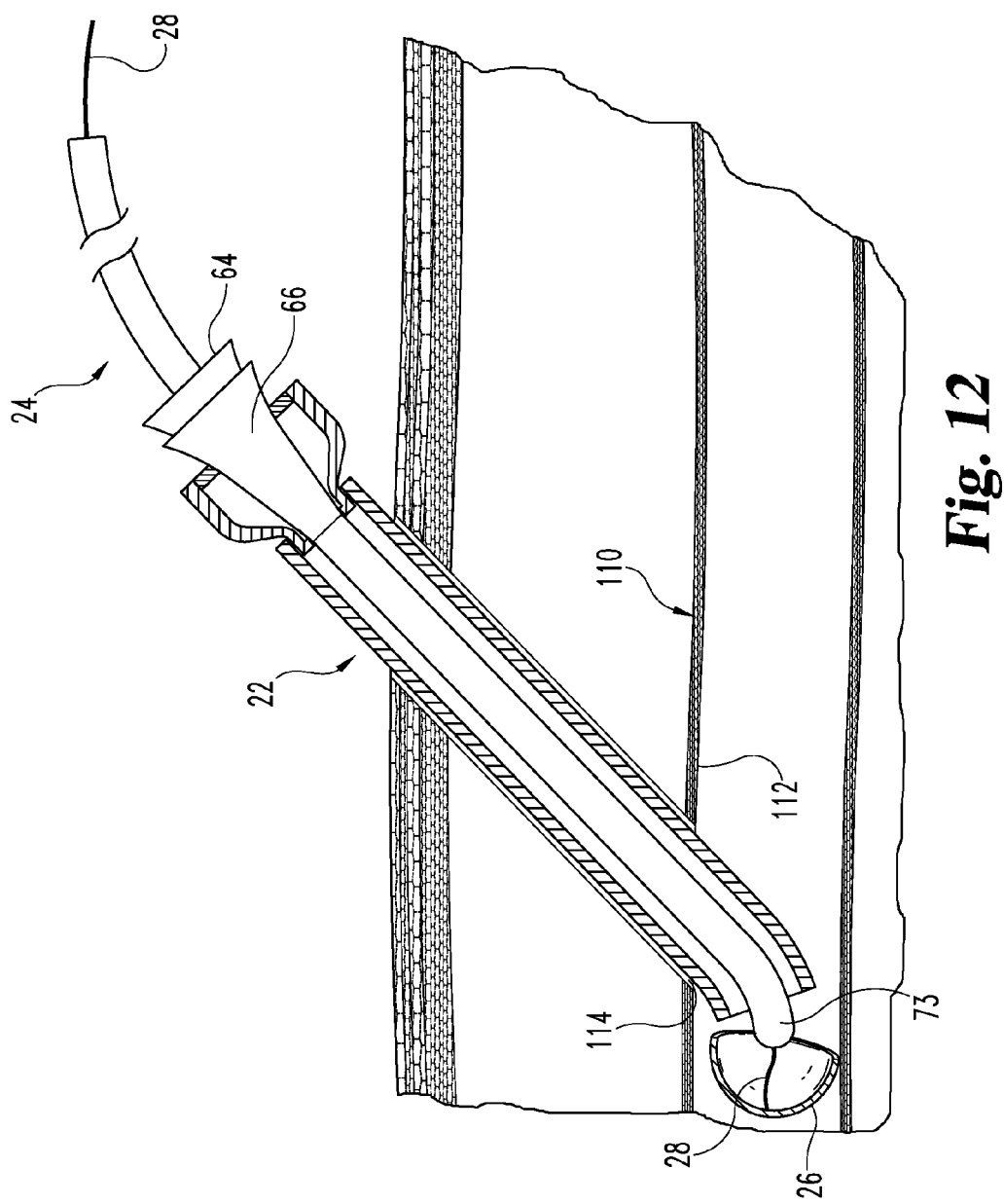
Figure 13:
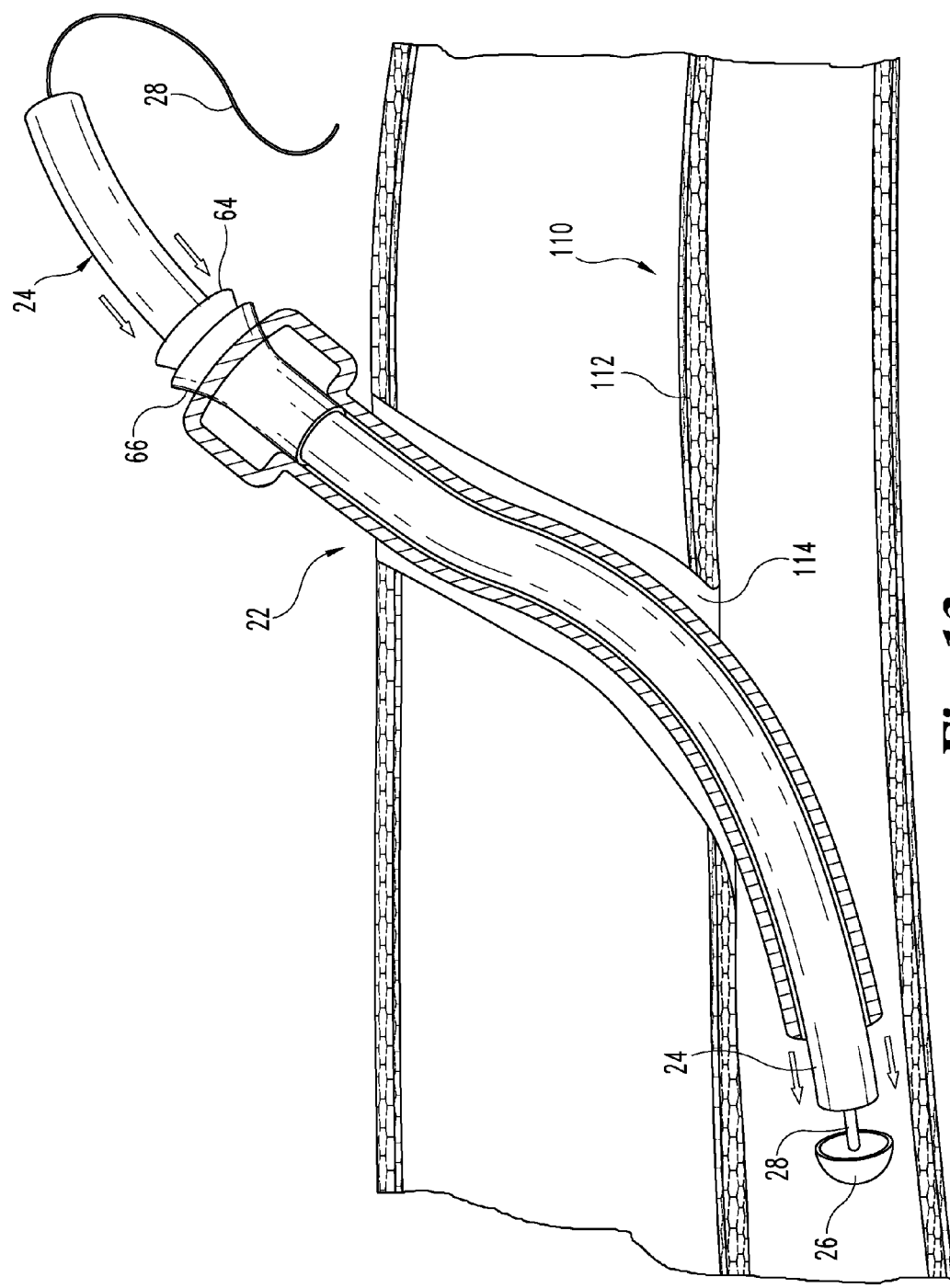
Figure 14:
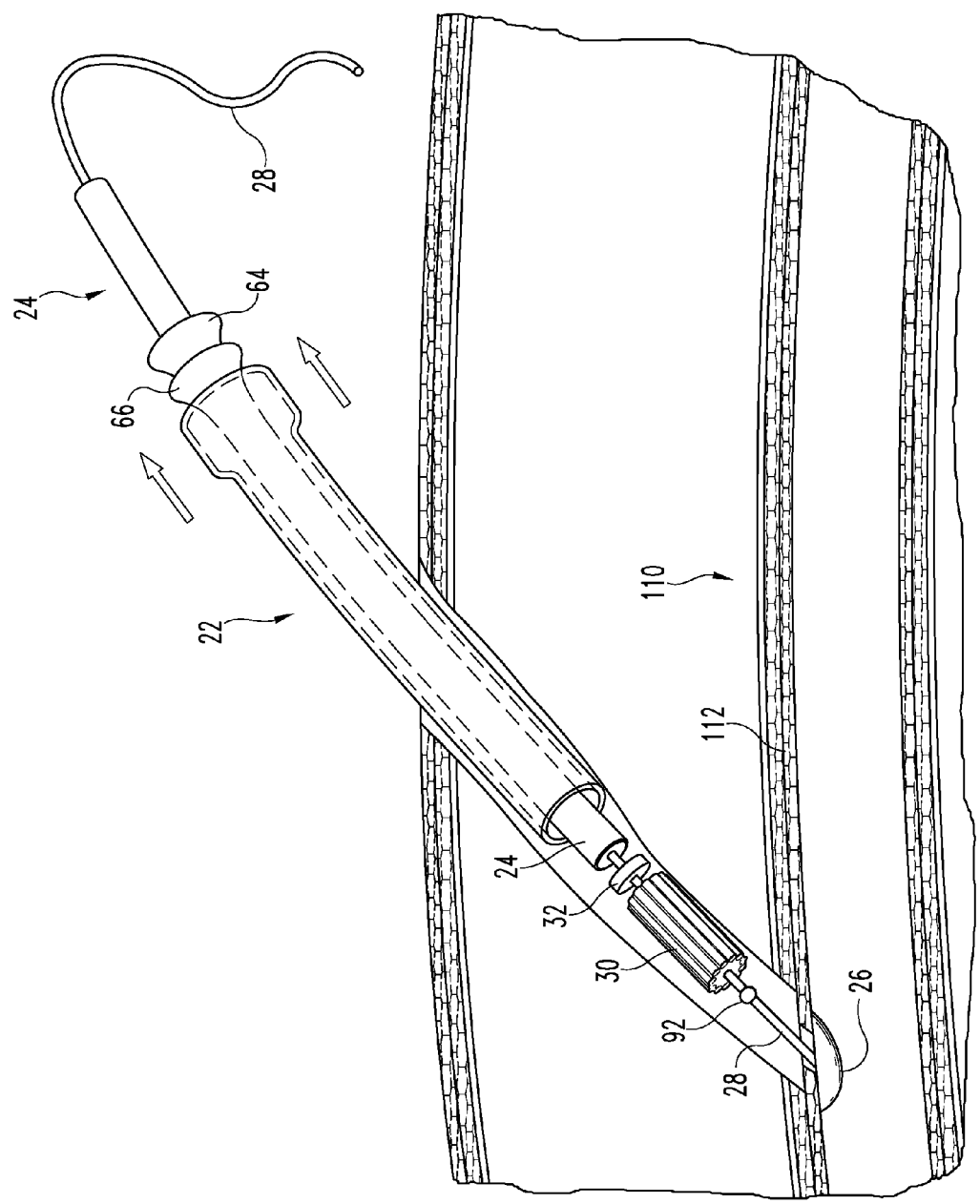
Figure 15:
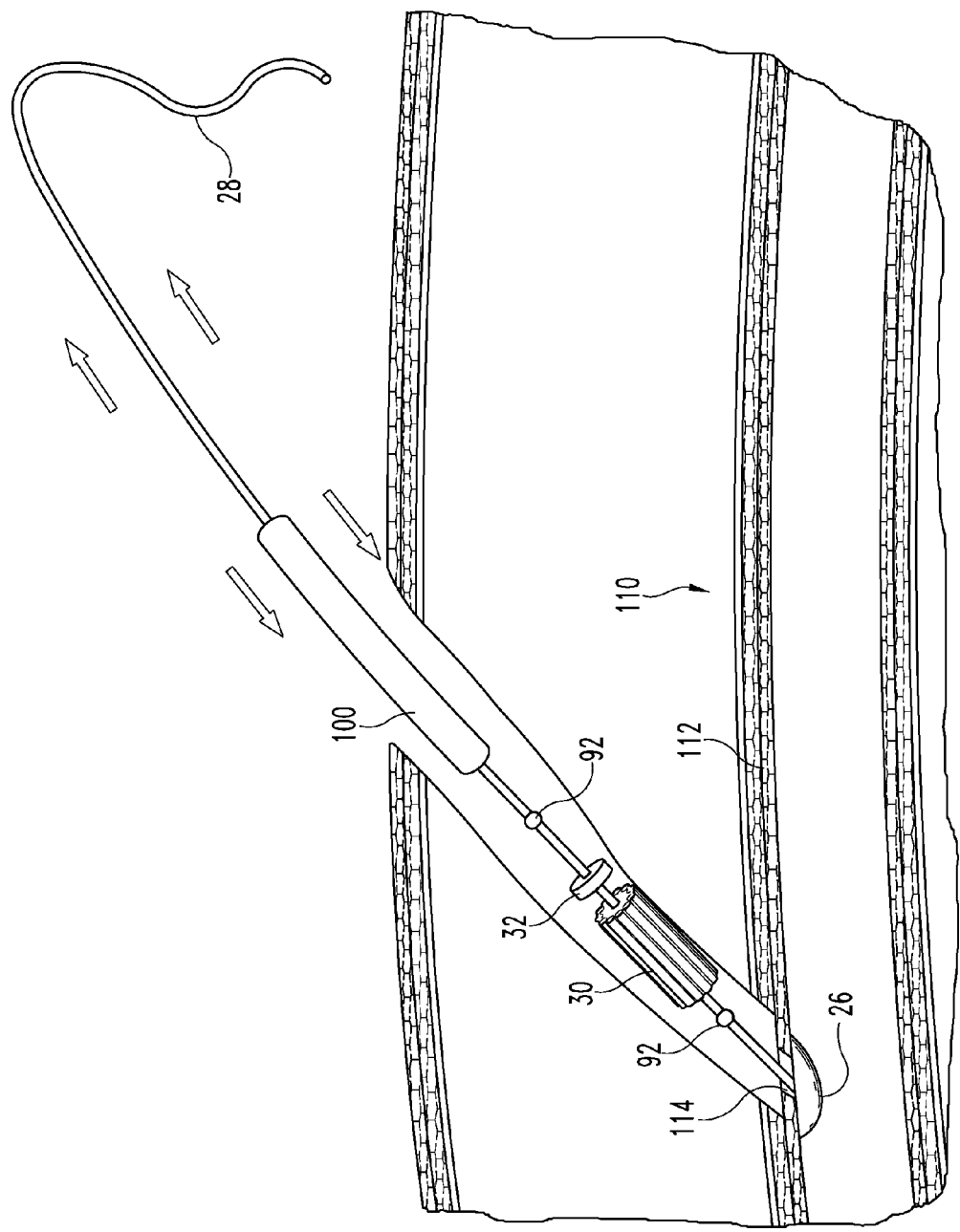
FIGS. 15-17 are views of a portion of the system of FIG. 1 in use in one embodiment.
Figure 16:
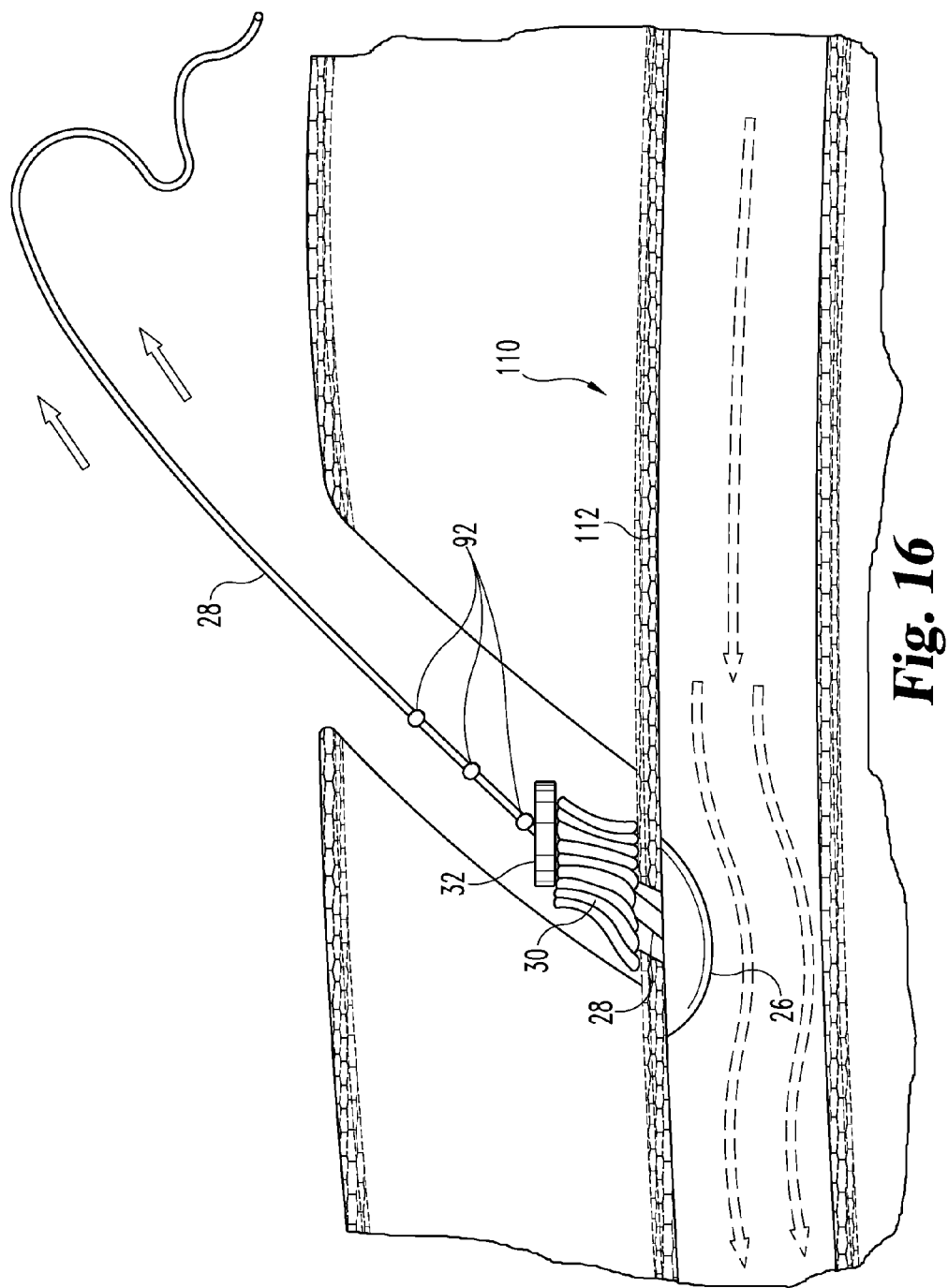
Figure 17:
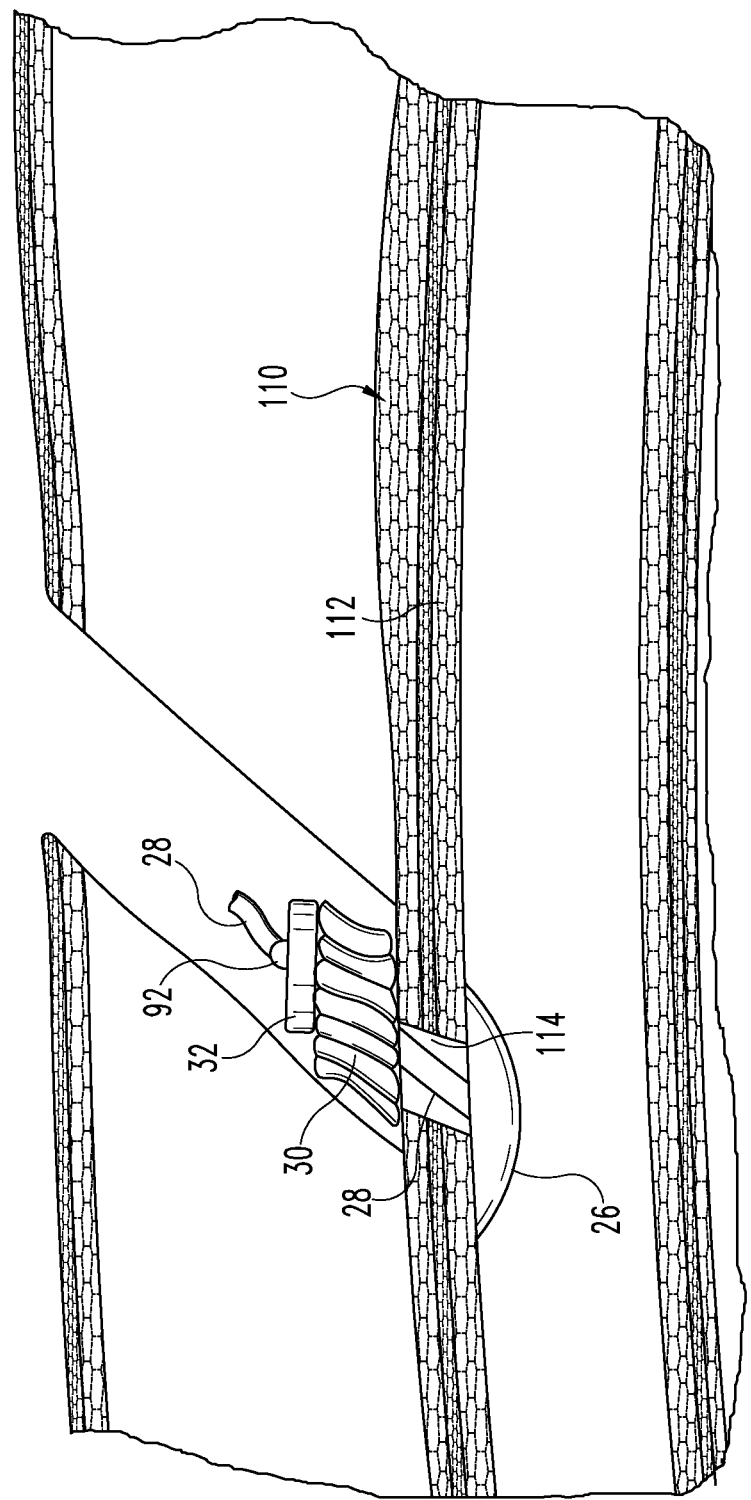

Seal 26 in the illustrated embodiment is a flexible dome having a thin wall 82. Wall 82 can have a constant or varying thickness, with wall 82 in certain embodiments having a maximum thickness in the range of about 0.0050 inches to about 0.050 inches, and in a particular embodiment about 0.015 inches. In the illustrated embodiment, the maximum thickness of seal 26 is in the middle, where filament 28 connects, and the thickness decreases uniformly out to a rim 84. Seal 26 is hemispherical or part-spherical in an unstressed state (e.g. FIGS. 5-6), having a circular or elliptical rim 84. Rim 84 is substantially in one plane in this embodiment, having little or no breadth. Seal 26 has an exterior convex surface 86 and an interior concave surface 88 which is open and unobstructed. In this embodiment, surfaces 86 and 88 have differing radii, so that they intersect or approach each other at rim 84, and a center point 90 has a tangent plane that is parallel to the plane of rim 84. Seal 26 in particular embodiments is a relatively shallow dome in its relaxed or unstressed state, defining a relatively small angle θ (FIG. 6) between the outer edge of peripheral rim 84 (e.g. between the surfaces 86 and/or 88 at rim 84) and center point 90 of the dome. In certain embodiments this angle θ is about 10 to about 80 degrees, for example about 25-40 degrees, or in particular embodiments about 30 degrees. The flexibility of seal 26 permits an elastic deformation or change in shape, for example as indicated in FIG. 7. Under stress, as discussed further below, seal 26 can flatten so that a portion 84a along rim 84 becomes planar or slightly concave, and in some embodiments portion 84a can curve concavely into the convex outer surface 86. Seal 26 can be constructed so as to completely flatten (e.g. surface 88 substantially conforming to surrounding tissue) under stress as experienced after implantation, or so as to not completely flatten under such stress, as discussed further below.

Filament 28 is a thin strand compared to seal 26 in this embodiment, for example a synthetic suture. It includes a series of stop elements 92 spaced at least along a distal region, in one embodiment evenly spaced as shown. Stop elements 92 are shown as bulbous, blunt structures such as beads that extend all the way around filament 28 and are formed as a monolithic part of filament 28 in this embodiment, for ease of manufacture, and also to reduce the likelihood of damage to other parts. It is to be understood that stop elements 92 may be of a variety of shapes, including barbs, knots, frusto-conical segments, or flat surfaces, and they may be made monolithically with the filament or separately from filament 28 and attached to it later. Filament 28 is attached at its distal end to the concave interior surface 88 of seal 26, and in particular embodiments is attached at center point 90. The distal-most of elements 92 is outside of rim 82 of seal 26 when filament 28 is taut. In particular embodiments, the diameter of filament 28 outside of stop elements 92 (e.g. above and below the end elements 92 and between individual pairs of elements 92 in the illustrated embodiment) is between about one-sixth and one-tenth (e.g. about one-eighth) the diameter of seal 26, the distal-most of stop elements 92 are between about 3 mm and 15 mm from the end of filament 28, and elements 92 are spaced between about 0.5 mm and 1 mm apart.

Buffer 30 can be an absorbent, biodegradeable, compressible biomaterial mass which surrounds filament 28 in this embodiment. While a variety of absorbent and/or biodegradeable materials could be used for buffer 30, it has been found that extracellular matrix material (ECM), such as small intestine submucosa (SIS), is quite effective in exhibiting the characteristics identified herein for buffer 30. Such material is prepared to be compressible in length, with such compression resulting in width expansion in some embodiments to fill or cover a percutaneous or other opening, is highly absorbent, and has tissue-regenerative properties that aid healing. Spongy or foam materials, sheet materials or other forms can be used. Preparation of such materials is disclosed in U.S. patent application Ser. No. 12/489,199 (filed Jun. 22, 2009 and incorporated herein by reference in its entirety). As noted above, in particular embodiments the material is a collagenous extracellular matrix material such as SIS, and it is treated to partially denature and expand the native collagenous structure, for example with sodium hydroxide, to provide desired porosity and/or foam characteristics when dried. In certain embodiments, the extracellular matrix material can be processed to be medically acceptable while retaining a native collagenous microarchitecture (e.g. a native sheet form) and endogenous bioactive substances from an animal source tissue, such as a porcine, ovine, bovine or equine source tissue. Such endogenous substances can for example include one, some, or all of growth factors (e.g. Fibroblast Growth Factor-2), glycosaminoglycans, and proteoglycans. The extracellular matrix material can be treated with a chemical crosslinking agent, for example glutaraldehyde or a carbodiimide, to add crosslinks over and above any native crosslinks present, or can lack any such treatment. In other embodiments, the buffer 30 can comprise a reconstituted collagen sheet or foam, optionally crosslinked with a chemical crosslinker such as those discussed above.

ECM material for use in the invention can be processed to be biodegradable by natural body processes. In one embodiment, buffer 30 is formed from a sheet of material folded, rolled and/or attached to itself to form an elongate body, the length of which is substantially larger than its diameter. As discussed further below, lengthwise compression of buffer 30 results in radial expansion, and so buffer 30 with such lengthwise compression and absorption of bodily fluids can effectively occupy a percutaneous opening in a patient communicating with an opening in a side wall in a vessel, in an example of a medical usage of system 20. The relative softness, compressibility and absorptive nature of the extracellular matrix material embodiment of buffer 30, noted above, is less harsh on the vessel wall than rigidly pressing items.

Another embodiment of buffer 30 includes a sheet or ribbon of biomaterial (such as SIS or other ECM material, as discussed above) through which a filament (e.g. filament 28) is threaded or woven. In particular examples, filament 28 may pierce the sheet at several places, or the sheet may have several holes (e.g. end-to-end perforations) for filament 28, so that filament 28 moves through the sheet from one side of the sheet to the other (e.g. FIG. 5A) one or more times. In such examples, the ribbon or sheet can be folded (e.g. with alternate folds opening in opposite directions) between such holes or other locations where filament 28 pierces the ribbon or sheet, presenting individual leaves between folds that can collapse or expand in an accordion-type configuration, to guide compression of buffer 30 as described below or its expansion in the body. In other examples, the process of forming the sheet includes incorporation of filament 28 into the sheet, as by forming the sheet around the filament or by attaching or pressing the filament into the sheet as it is formed or dried (e.g. FIG. 5B).

In a first condition, the sheet of buffer 30 remains substantially flat or slightly undulating, with filament 28 running along or through it. Buffer 30 can be placed into delivery tube 24 in a flat, rolled, folded or other condition. With filament 28 running along or through buffer 30, any folding or compressing of buffer 30 in loading into delivery tube should not longitudinally fold or compress the buffer 30, so that filament 28 can remain substantially along the longitudinal axis of delivery tube 24 and under tension in use, as described herein. As described herein, locking disk 32 is along filament 28 and proximal of buffer 30. When placement of buffer 30 and locking with disk 32 is desired, disk 32 is pushed along filament 28 to compress the elongated ribbon or sheet of buffer 30. In so doing, the ribbon or sheet of buffer 30 crumples or folds along filament 28, i.e. at least portions of buffer 30 move with respect to tensioned filament 28, into at least an approximation of an accordion fold. If retainer disk 33 is used, such crumpling or folding occurs between disks 32 and 33. The crumpling or folding provides a flattening of the elongated ribbon or sheet of buffer 30, to cover or fill an opening in tissue as the physician desires. Expansion of buffer 30 in width or a lateral dimension can occur if buffer 30 is prepared and/or placed for such expansion.

Such an accordion-fold arrangement of buffer 30 provides an original elongated condition of buffer 30 (e.g. an elongated ribbon) for ease of placement in system 20 and insertion into the body, and also provides easy and controlled compression of buffer 30 to or toward a disk or a box-like configuration in use. For an opening desired to be filled, such as a vesicovaginal or other fistula, the elongated buffer is moved into the opening, and compression of the buffer to a desired degree results in the buffer assuming a box- or capsule-like shape to occupy at least a significant portion of the volume of the opening. The buffer need not be compressed to a smallest volume or height, with layers or portions of buffer material in close contact with layers or portions above and/or below them, but may be left at least slightly unfolded or expanded within the opening. For an opening to be covered, such as an access opening in the side of a blood vessel, fuller compression accordion-folds or crumples the buffer against the tissue (or against retainer disk 33 if present), presenting a flatter buffer.

Locking disk 32 is substantially circular, flat and thin in the illustrated embodiment, although other configurations may also be used. A hole 96 is in the center of disk 32, with hole 96 having a diameter slightly less than an outer dimension (e.g. a diameter) of stop elements 92 of filament 28. In particular embodiments, part or all of hole 96 can be covered or filled with material, for example a relatively thin cover 97 that is scored to form a ratchet-type mechanism that permits stop elements 92 to pass through disk 32 when disk 32 is moved along filament 28, but opposes or prevents movement of elements 92 back through disk 32 in the opposite direction. In embodiments in which hole 96 is completely open, it is sized so that stop elements 92 can be forced through, e.g. with slight compression of elements 92 or slight enlargement of hole 96, but elements 92 cannot easily pass through hole 96 without any contact.

In some embodiments, a retainer disk 33 is also provided (e.g. FIG. 4). Retainer disk 33 is substantially identical in one form to locking disk 32, and for brevity the above discussion will not be repeated. Disk 33 may be flexible and at least slightly larger in diameter than the inner diameter of delivery tube 24 in some embodiments. In certain uses or therapies, it was found that buffer 30 could migrate toward seal 26 during manipulation of seal 26, filament 28 and/or other parts of system 20. To prevent or limit movement of buffer 30, retainer disk 33 may be placed on filament 28 (with filament 28 extending through the hold of retainer disk 33 in the same way as it does with respect to locking disk 32) between seal 26 and buffer 30, with disk 33 held on filament 28 by a stop element 92. Disk 33 controls buffer 30 (e.g. by limiting or preventing movement of buffer 30 distally toward seal 26) during positioning of seal 26. For example, disk 33 may keep buffer 30 from moving out of or escaping delivery tube 24 until pushed. As will be noted below, once seal 26 is placed to cover the hole to be sealed, retainer disk 33 with buffer 30 and locking disk 32 is moved forward over filament 28 and into position to hold seal 26 in place. In these embodiments, tissue (e.g. vascular tissue or a portion of the tissue through which a fistula extends) is compressed or otherwise between retainer disk 33 and seal 26. Thus, in embodiments including retainer disk 33, it remains between at least a portion of buffer 30 and one or both of tissue and seal 26 prior to and during use.

By holding or retaining buffer 30 within delivery tube 24 while seal 26 is placed, retainer disk 33 reduces substantially the amount of blood, interstitial fluid, or other fluids that come in contact with buffer 30 prior to locking seal 26 in place. It has been found that maintaining buffer 30 as dry as possible provides for more controlled moving and placement of buffer 30 during the locking process. In addition, use of a retainer disk 33 allows retainer disk to essentially clear a path for buffer 30 through layers of tissue. It has been found that without retainer disk 30, at times the friction or interference of forcing buffer 30 through multiple layers of tissue can disorient, remove part(s) or otherwise damage buffer 30, in addition to providing opportunity for buffer 30 to take in liquid or become saturated prior to final locking.

In embodiments for use in a human or animal body, the repair structure that remains inside the body—seal 26, filament 28, buffer 30 and locking disk 32 (and retainer disk 33 if present) or other compression member—can be made of biodegradable polymers or other materials so that they are resorbed by the body after the vessel with which they are used has been repaired. For example, filament 28 and seal 26 may be made of polyglycolic acid polymer and/or polycaprolactone. Disk 32 is made of the same material as seal 26, in particular embodiments, or can be made of other resorbable materials. Examples of desirable materials for buffer 30 are discussed above. As previously noted, the thickness of seal 26 is chosen in association with the material used for it to provide flexibility, especially along rim 82 and allowing seal 26 to be folded for insertion into delivery tube 24, along with resilient strength to prevent full collapse of the center of seal 26 during use, and/or to provide spring force which resiliently urges rim 82 against the vessel wall when the seal 26 is forced to a partially or fully flattened state by tension applied by filament 28.

A pusher 100 may also be provided in connection with the delivery tube 24 and the structure for sealing. In the illustrated embodiment, pusher 100 is a cylindrical tube of rigid or sturdy material, and has an inner lumen that is at least slightly larger than stop elements 92, so that pusher 100 can travel relatively freely along filament 28. In a particular embodiment, the inner diameter of pusher 100 is smaller than at least part of the most distal stop element 92. Pusher 100 also has an outer diameter that is smaller than the lumen 68 of delivery tube 24, or at least smaller than the opening through the skin of a patient. In the illustrated embodiment, pusher 100 is relatively short compared to the overall length of delivery tube 24. In other embodiments, pusher 100 is substantially longer, so as to extend out of the patient after delivery tube is removed, or to extend from delivery tube 24 after tube 24 has been retracted sufficiently to expose locking disk 32. Such embodiments of pusher 100 are of a plastic or other material that maintains its rigidity over a sufficient length (e.g. 10 to 20 cm or more), so that manipulation of the pusher 100 within the patient is not necessary. When pushing of locking disk 32 to lock seal 26 is desired, the user can manipulate such longer embodiments of pusher 100 from outside of the patient, with tactile feedback indicating passage of locking disk over one or more stop elements 92.

To prepare delivery tube 24 for use, seal 26, filament 28, buffer 30 and disk 32 (and retainer disk 33, if used) or other compression member are assembled with delivery tube 24. As noted above, filament 28 is previously fixed to interior concave surface 88 of seal 26. Buffer 30 is placed around filament 28 (or filament 28 is threaded through buffer 30) so that buffer 30 is above or adjacent to one or more stop elements 92 on filament 28. Locking disk 32 is placed on filament 28, with filament 28 extending through hole 96 in disk 32, so that disk 32 is proximate buffer 30. Disk 33 (if present) is likewise placed on filament 28 so that it is between buffer 30 and seal 26 and held on or above a stop element 92. If used, pusher 100 is also placed on filament 28 proximate disk 32, again so that filament 28 extends from pusher 100. The above preparations can be made prior to insertion of any of the parts into delivery tube 24, or some or all items (particularly disk 32 and pusher 100) may be advanced along filament 28 after seal 26 and filament 28 are within delivery tube 24.

In a particular embodiment, filament 28 is inserted through lower boss 66 and/or distal opening 72 of body 62 of delivery tube 24, and is threaded through lumen 68 and out through proximal opening 70. Seal 26 is folded and inserted into lower boss 66, and any slack is taken out of filament 28. In its folded condition, seal 26 is under stress and tries to regain its unstressed state, and so it is in affirmative engagement with the inside of boss 66. If buffer 30, disk 32, disk 33 and/or pusher 100 were pre-placed on filament 28, then they precede seal 26 in insertion into lower boss 66 and on into body 62 of delivery tube 24. If buffer 30, disk 32, disk 33 and/or pusher 100 were not pre-placed, then they can be advanced over filament 28 and through proximal opening 70 of tube 24. One embodiment of delivery tube 24 prepared for use is seen in FIGS. 1 and 4, and FIG. 4 indicates relative positions of seal 26, filament 28, buffer 30, disk 32, disk 33 (if used) and pusher 100.

The use of system 20 (particularly delivery tube 24 with or without sheath 22) will now be described with respect to closing and repairing an opening in a wall of a blood vessel. As noted previously, it is to be understood that similar usages can be made in other body tissues (e.g. bile or other ducts), or other vessels, conduits or walls. For example, in use with fistulae (e.g. a vesico-vaginal fistula), seal(s) as described herein may be placed and held over fistula openings and against tissue substantially as described below, with buffer material within the fistula to assist with healing or correction of the fistula.

A surgeon or other medical professional performs and completes desired procedure(s) that involve access to the blood vessel 110 through its wall 112 (e.g., balloon catheterization or stenting procedures). If a sheath, cannula or other access device or portal was used for the procedure(s), it can be left in the vessel, and prepared delivery tube 24 is inserted through it, as further discussed below. If no such access device is present, or if a change of access device is necessary or desired, sheath 22 is placed in the opening 114 by using a dilator with an introducer sheath so that distal end 42 is inside the vessel. Proximal opening 48 with seal 58 provides a barrier for blood that enters sheath 22.

Delivery tube 24, prepared as noted above, is inserted into head portion 38 of sheath 22. Specifically, cylindrical part 78 of lower boss 66 enters head portion 38 and lodges in lower opening 52 of head portion 38 to form a close fit or seal, while flared part 80 of lower boss 66 engages head portion 38 (as indicated above), which also may form a closure or seal. Pushing delivery tube 24 forward causes sliding of body portion 62 through lower boss 66, since head portion 38 blocks further forward motion of lower boss 66. Body portion 62 is pushed forward until upper boss 64 engages lower boss 66, which prevents further forward travel of delivery tube 24 with respect to sheath 22.

Once flared portion 80 of lower boss 66 engages head portion 38, and distal end 73 of body portion 62 slides through lower boss 66, end 73 contacts seal 26 and pushes it out of lower boss 66. As seal 26 leaves lower boss 66, seal 26 expands at least slightly toward its unstressed or unfolded configuration until it contacts the interior of sheath 22. As body portion 62 is further advanced, its distal end 73 continues pushing seal 20 along sheath 22. With bosses 64 and 66 engaged, end 73 of delivery tube 24 (and consequently seal 26) is beyond the end of sheath 22. When seal 26 exits sheath 22, it expands to its non-stressed or original shape (e.g. part-spherical). Throughout the advancing of delivery tube 24 through sheath 22, the user should maintain tension on filament 28, so that as seal 26 exits sheath 22 it will remain close to or against distal end 73 of tube 24 and/or end 50 of sheath 22. In this way, entry of blood into the concave side of seal 26 is limited or prevented, along with potential drift of seal 26 due to flow of the blood or potential blockage of flow by seal 26.

With tension being maintained on filament 28, sheath 22 is then removed from the patient. For example, head portion 38 of sheath 22 can be gripped and pulled. That pulling force is transmitted via head portion 38 and bosses 64, 66 to body portion 62 of delivery tube 24, resulting in withdrawal of delivery tube 24 along filament 28 with sheath 22. As tube 24 and sheath 22 are initially withdrawn, tension on filament 28 maintains seal 26 close to or in contact with end 73 of tube 24 and/or end 50 of sheath 22 until tube 24 exits vessel 110. Sheath 22 first exits vessel 110, resulting in a reduction in the size of opening 114 due to the elasticity of vessel tissue. Vessel tissue contracts toward or against distal end 73 of body portion 60. As tube 24 exits the vessel, some additional contraction of opening 114 may occur, and rim 84 of seal 26 contacts the inner surface of vessel 110 surrounding opening 114.

As rim 84 contacts the vessel, seal 26 provides a fluid-tight barrier around opening 114. Tension applied to filament 28 may be continued or increased so as to deform seal 26 at least partially (e.g. FIG. 7) and potentially so as to pull substantially the entire inner surface 88 flush against the inner surface of vessel 110. In this manner, the seal 26 can be implanted and secured in a stressed state by which its tendency to return to its concave, unstressed state will urge rim 84 against the vessel surface to facilitate the formation of a seal and/or to resist curling or lifting of the outer periphery of seal 26 into the lumen of the vessel 110. With seal 26 maintained against tube 24 and/or sheath 22 on insertion and withdrawal until seal 26 contacts the vessel, a minimum amount of blood is lost through opening 114. Sheath 22 and tube 24 occupy opening 114 while they are present in the vessel, so that blood can escape only through any gaps that may form between the vessel and sheath 22 or tube 24, as when they exit vessel 110 and opening 114 contracts. Maintaining seal 26 in contact with tube 24 and/or sheath 22 results in a minimum amount of blood in the concave portion of seal 26 and thus a minimum amount of blood escaping through opening 114 from within the concave portion of seal 26 or from under rim 82 as seal 26 contacts the vessel.

In certain embodiments, the entirety of seal 26 will not lie along the inner wall surface of vessel 110. Rather, in these embodiments, at least a portion of concave surface 88 is separated from the internal vessel wall. Convex surface 86 maintains smooth fluid flow by virtue of its rounded surface. Such fluid flow along convex surface 86 can also provide affirmative pressure, helping to maintain rim 82 and adjacent surface area of seal 26 against the vessel. Further, the tension of filament 28 is transmitted to the middle of seal 26, which remains above the level of the vessel wall. Accordingly, the force on seal 26 is focused through rim 84, pressing rim 84 (and in some embodiments an annular portion of seal 26 adjacent rim 84) approximately perpendicularly against the vessel wall. The domed shape of seal 26 provides a secure seal with better force transmission than if the entirety of seal 26 remained against the vessel wall.

With seal 26 engaging the interior of the vessel around opening 114, as discussed above, withdrawal of sheath 22 and tube 24 continue until they are completely free of filament 28 (i.e. the distal end of filament 28 exits distal ends 73 and 50 of tube 24 and sheath 22). To maintain tension on filament 28, the user may hold filament 28 toward its distal end as withdrawal of sheath 22 and tube 24 begins, and as they move beyond the patient's skin the user can change the hold of filament 28 to a point between sheath 22/tube 24 and the skin. As tube 24 is withdrawn, disk 33 (if present), buffer 30, and disk 32 remain on filament 28 within the patient. Sheath 22 and tube 24 may be put aside or discarded when free of filament 28.

Disk 32 is then moved along filament 28 to push buffer 30 (and disk 33 if used) toward or against the external surface of vessel 110. In embodiments in which pusher 100 is provided, it can be held or gripped by the user (directly or by a gripping device) and moved forward against disk 32. Forcing disk 32 and buffer 30 forward (with or without disk 33) results in compression of buffer 30 between disk 32 and the exterior of vessel 110 (or between disks 32 and 33, if disk 33 is used), resulting in buffer 30 covering or overlying opening 114 in vessel 110, and in configurations of buffer 30 in which its widening is possible, widening buffer 30 within the patient. In particular embodiments, buffer 30 occupies most or all of the space in percutaneous opening 116. Buffer 30 absorbs fluid, including blood that may escape from opening 114 during use of system 20, as well as blood, interstitial or other fluids from the skin surrounding percutaneous opening 116 as it moves through opening 116 and is compressed against the exterior of vessel 110. Disk 32 moves over one or more stop elements 92 of filament 28 as it compresses buffer 30, and in a particular embodiment when disk 32 is in its final position there are no stop elements 92 between it and seal 26. Tension in filament 28 is thus maintained by disk 32 and the element 92 that keeps disk 32 from moving back up filament 28, so that buffer 30 remains compressed between disk 32 and disk 33 and/or vessel 110, and so that seal 26 remains affirmatively engaged with the inside of vessel 110 around opening 114.

Seal 26 operates to cover opening 114 on the inside of vessel 110, to prevent fluid from approaching opening 114. Buffer 30 is pressed against vessel 110 (or disk 33) and absorbs fluid that may escape through opening 114 as seal 26 is being placed as well as interstitial or other fluids as it expands and fills all or part of percutaneous opening 116, as previously indicated. The tissue-regenerating nature of buffer 30 (e.g. an angiogenic nature) helps tissue regrow through it and in or across percutaneous opening 116, as well as assisting healing of vessel 110. Buffer 30 does not extend through opening 114 into the lumen of vessel 110 in the illustrated embodiment. As noted above, the implanted items can be made of bioresorbable material to allow them to be resorbed by the body over time, so that no foreign material remains in the body after healing is complete.

When disk 32 is moved sufficiently or as desired to maintain the above-noted respective positions and relationships of seal 26 and buffer 30 with respect to vessel 110, filament 28 can be cut above disk 32 and the now extraneous portion of filament 28 discarded. Appropriate antibiotic or other medicaments can be applied in or to percutaneous opening 116, and an appropriate dressing may be placed over that opening.

Devices substantially according to the above-noted embodiments have been tested in a pig model. The pig model has both similarities to human anatomy, and some difficulty insofar as spasms in the tissues can tend to dislodge devices within a vascular wall opening and/or enlarge the opening. A number of devices were introduced into relatively small blood vessels (generally 6-7 mm in diameter) substantially according to the methodology noted above. Commonly, when a sheath is removed from a vessel and plugs or pressure are applied to close the vessel wall opening, a gush or spurt of blood occurs at least initially until the plug or pressure is in proper place or form. On withdrawal of the sheath and tube in testing the embodiments of this disclosure, no gush or spurt of blood was observed, even in cases in which tissue spasm(s) in the pig model occurred.

As suggested above, it is to be noted that delivery tube 24, packed with seal 26, filament 28, buffer 30 and disk 32 (and disk 33 if used), can be used with sheath 22 provided with system 20, or with another sheath, e.g. one already within the vessel as a part of a prior procedure. Using the human body as an example, it is known to place a cannula or sheath through the skin and into a blood vessel. The sheath is used to pass a balloon catheter or other device into the vessel and to an operative or treatment site. After removal of the balloon catheter or other device, a delivery tube 24 with structures 26, 28, 30, 32, and/or 33 can be inserted directly into the already-placed sheath for use as described above. Thus, it may not be necessary to provide a sheath 22 with delivery tube 24, or to use the sheath provided with delivery tube 24, in closing the vascular access. The flared configuration of boss 64 of delivery tube 24 can be accommodated by sheaths of various opening diameters associated with a variety of devices or manufacturers, with the flare provided a close, sealing fit with any of such opening diameters.

In a particular embodiment, bosses 64, 66 have engaging structure (e.g. tongue and groove structure) that click or snap together when tube 24 is fully inserted through sheath 22. As one example (FIG. 10), the outside of upper boss 64 may have at least one ridge or protrusion R around its circumference, and the inside of lower boss 66 may have at least one complementary groove or indentation G. The user knows that tube 24 is fully inserted, i.e. seal 26 and end 73 are sufficiently beyond end 50 of sheath 22, when he or she hears or feels the click or snap of engagement of protrusion R in indentation G.

Another embodiment of a seal 26' is shown in FIG. 8. Seal 26' is substantially identical to seal 26 in most respects, including a thin wall 82', rim 84', convex exterior 86', and concave open interior 88' fixed to filament 28. Around rim 84' and/or a portion of concave interior surface 88' are one or more beads 89'. In the illustrated embodiment, bead(s) 89' are rounded or part-cylindrical and extend around the entirety of seal 26'. As seal 26' is drawn into contact with the inside wall of vessel 110, bead(s) 89' come into contact with the vessel wall to seal opening 114 away from flow. With bead(s) 89, pressure on seal 26' is focused in the small surface area of the connection between bead(s) 89' and the vessel wall. Presence of such bead(s) can reduce the amount of tension needed on filament 28 to maintain the seal of seal 26'.

Referring now generally to FIG. 8A, there is shown a particular embodiment of a monolithic seal 126 and filament 128. Filament 128 and seal 126 are manufactured together in one piece, of a single material, in a particular embodiment. Seal 126 is very similar to the embodiment of resilient seal 26 described above, with similar features having numbers increased by 100, and may include features discussed with respect to seal 26. Seal 126 in this embodiment is a flexible dome having a thin wall 182, which has a first thickness where it joins filament 128 and tapers in thickness radially outward to rim 184. Seal 126 has an exterior surface 186 that is initially (unstressed) convex and an interior surface 188 which is initially concave and open and unobstructed. A center point 190 has a tangent plane parallel to the plane of rim 184. The flexibility of seal 126 permits some change in shape, particularly proximate to rim 184. Under stress, as discussed further below, seal 126 can flatten so that seal 126 or at least a portion at or adjacent rim 184 becomes planar or slightly concave. Because of the initial unstressed form of seal 126, when seal 126 flattens or partially inverts against a vessel (e.g. so that exterior surface 186 has a concave portion), the edges of seal 126 adjacent rim 184 are pressed against the vessel, somewhat in the manner of a leaf spring. Seal 126 can be constructed so as to not completely flatten under stress as experienced in the vessel, as discussed further below, but maintains at least a portion in a domed or part-spherical condition.

Filament 128 is very similar to the embodiment of filament 28 described above, with similar features having numbers increased by 100, and may include features discussed with respect to filament 28. Filament 128 is a thin strand in this embodiment, having a series of frusto-conical portions 192 spaced along a distal region, in one embodiment evenly spaced as shown. Portions 192 function generally as pawls, and in the illustrated embodiment each has a conical exterior 192a that widens toward seal 126 and an end surface 192b that faces seal 126 and is substantially perpendicular to the longitudinal axis of filament 128. Portions 192 are formed as a monolithic part of filament 128 in this embodiment, for ease of manufacture, and also to reduce the likelihood of damage to other parts. It is to be understood that portions 192 may be of a variety of shapes, such as rounded, spherical or part-spherical pips or knobs or others as indicated above with respect to filament 28, and they may be made separately from filament 128 and attached to it later. Filament 128 is monolithically attached in the illustrated embodiment to the interior surface 188 of seal 126, and in particular embodiments is attached at center point 190 (e.g. thickest portion of seal 126).

The distal-most of portions 192 is outside of rim 182 of seal 126 when filament 128 is taut. The illustrated embodiment also provides a short length of constant-diameter filament 128 (as at locations 193) between the end 192b of one portion 192 and the beginning of the conical exterior 192a of an adjacent portion 192. In particular embodiments, about one-eighth inch is the distance between end surface 192b of distal-most portion 192 and the plane of rim 184 in the unstressed initial configuration of seal 126. An enlarged portion or knob 194 is at the proximal end of filament 128, and includes a through-hole 195. An additional length of filament, which can be another piece such as a length of suture, can be looped through our attached through through-hole 195, and serve in the overall filament of the system which includes the filament 128 and the additional attached length of filament.

As indicated above, filament 128 may be of the same material and may be monolithically formed with seal 126. As with seal 26, embodiments of seal 126 (and thus filament 128) made of polyglycolic acid polymer and/or polycaprolactone (or other biodegradable polymers or resorbable materials) are solid so as to limit or prevent fluid flow through an opening yet resiliently flexible to allow inversion or changes in shape to cover an opening with minimal interference. Accordingly, filament 128 of the same material will exhibit the same or similar characteristics, such as firmness (as opposed to the floppiness of a suture) and ability to transmit pushing force with bendability or flexibility, akin to the stem of a leaf. The illustrated embodiment shows that such a stem may be cylindrical and substantially straight in an unstressed condition, but such flexibility naturally permits insertion through an introducer or other tube into a bodily vessel or other tissue. The enlarged portion or knob 194 is shown in one embodiment in a spherical or part-spherical configuration, with through-hole 195 along a diameter of such a spherical or part-spherical configuration. In particular embodiments, portion 194 may have flat surfaces that are substantially perpendicular to hole 195, which may be desirable in limiting the amount of material used and the overall outer diameter. Similar embodiments may have a toroidal or donut-shaped portion 194. In this embodiment, knob 194, filament or stem 128 and seal 126 are a single closure piece 129.

Dimensions and materials for filament 128 may be similar or identical to those noted above. In some embodiments, the length of filament 128 (between the outermost points of knob 194 and seal 126) is sufficient so that a part of filament 128 extends out of the skin, e.g. between 1 and 2 inches, and in a particular embodiment about 1.6 inches. In other embodiments, the length may be such as to remain inside the body, for example less than one inch, or about three-quarters of an inch to one inch.

As indicated above, a suture 198 or other separate and detachable filament may be inserted through hole 195 of knob 194. An example of such a configuration is shown in FIG. 8B, which illustrates the embodiment of FIG. 8A along with examples of features indicated above. Suture 198 is looped through hole 195 so that separate portions 198a and 198b extend substantially parallel to each other and in a direction substantially away from seal 126. Suture 198 extends through a buffer 130, an end cap or locking cap 132, and a pusher 200, similar or identical to embodiments described above. Buffer 130, for example, may be similar or identical to embodiments of buffer 30, in which SIS and other ECM materials are considered highly useful, and such materials can be arranged so that suture 198 penetrates or goes through buffer 130. Likewise, cap 132 may be similar or identical to embodiments of locking disk 32 and pusher 200 may be a tubular member as discussed above with respect to pusher 100. As with the above embodiments, it will be seen that suture 198 (e.g. portions 198a, 198b) pass through cap 132 and pusher 200, in substantially the same way that filament 28 passes through disk 32 and pusher 100.

Seal 26, 126 can be of a number of sizes or shapes that have particular usefulness. A circular seal 26, 126 is indicated in the illustrated embodiments, which provides ease of manufacture and usability with a number of openings, such as generally circular openings associated with needles, introducers or cannulas. Oval seals can provide for closure or openings that extend further along a vessel (or other tissue) than around it. Teardrop-shaped seals, in which one lateral side is rounded like the circular or oval shapes and the other lateral side comes to a sharp or rounded point, or leaf-shaped or diamond-shaped seal in which both lateral sides come to such sharp or rounded points, may be useful in situations where the opening to be closed is in a narrow location, or in which the vessel (or other tissue) narrows to one or both sides of the opening. A compound-circle shape for a seal, in which a central circular or part circular seal portion has one or more additional circular or part circular seal portions on one or both lateral sides of the central portion, covers additional length of a vessel or multiple openings. As noted, elongated seals are useful for sealing larger vessels or larger openings.

Using the example of blood vessels, depending on the circumference of the vessel and the configuration of the seal 26, 126, the seal can extend around a portion of the inner circumference of the vessel, all or essentially all of such circumference, or can overlap a portion of itself within the vessel. For instance, a circular seal having a diameter that is the same as or substantially the same as the circumference of the vessel will, when pressed against the wall of the vessel to seal an opening in the vessel wall as indicated above, extend around all or substantially all of the circumference, so that diametrically opposed parts of the seal (prior to insertion) face or abut each other along the same portion of the vessel. Similarly, an oval-shaped seal having a minor axis with a length that is substantially equal to the inner circumference of the vessel but a larger major axis will have opposed portions on the minor axis that face or abut each other when the seal is pressed against the outer wall. The longer major axis extends along the vessel wall, to the longest extend at a position on the vessel diametrically opposed to the position where the parts of the seal on the minor axis face or abut each other. Such a seal can close a longer opening in the vessel without overlapping parts of the seal in an area of the vessel away from the opening. Where the diameter of the seal is greater than the inner circumference of the vessel, then a portion of the seal will overlap on itself when pulled against the vessel wall. Thus, seals 26, 126 may be provided with a maximum diameter or a maximum-length minor axis and variations in the length of the major axis, so that a seal will be available to seal larger holes while preventing or reducing the chance of overlapping itself, where such overlapping is undesirable.

Figure 18:
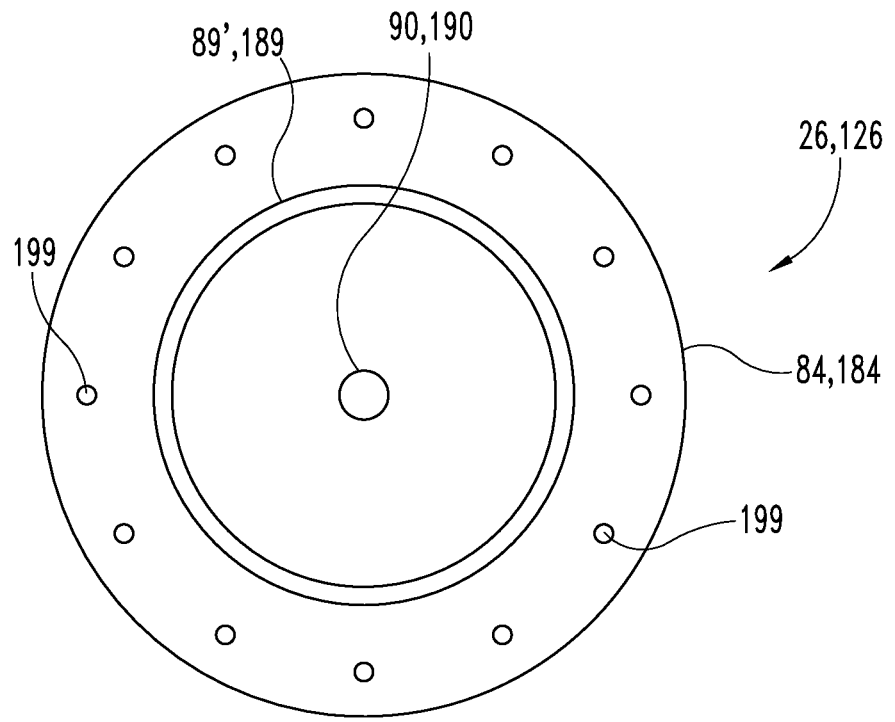
FIG. 18 is a plan view of a portion of an embodiment of a seal member described herein.
Figure 19:
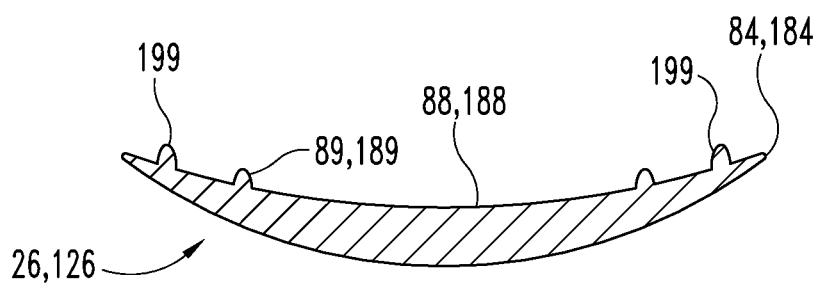
FIG. 19 is a side cross-sectional view of a portion of an embodiment of a seal member described herein.

Examples of seals 26, 126 may include additional features that assist in anchoring or maintaining the position of the seal with respect to a vessel or other tissue. As discussed above, a raised bead or ring 89', 189 may be provided within seals 26, 126 (e.g. along the inner concave surface 88, 188 or adjacent or along rim 84, 84', 184). It will be understood that multiple such beads may be provided which are concentric around suture or filament 28, 128. Further, raised portions similar or identical to those used for rings 89', 189 may extend substantially linearly or in chevron fashion from or pointing toward the center of seal 26, 126. The profile of ring 89', 189 is shown in FIGS. 18-19 to be substantially rounded or toroidal (e.g. semi- or part-circular in cross-section), and it will be understood that other profiles such as an oval, dentate, triangular or undulating profile may be used for rings 89', 189. Bumps, barbs or protrusions may also be provided in the inner concave surface 88, 188 of seal 26, 126 or around its rim 84, 184. Each of such bumps, barbs or protrusions may be monolithic and of the same material as seal 26, 126 so that they will also resorb. Barbs 199 (shown in an example in FIGS. 18-19) include a slimmer or pointed tip and a broader base attached to the seal 26, 126. Such barbs may be curved or otherwise directed inward (i.e. generally toward filament 28, 128), curved or otherwise directed outward (i.e. generally away from filament 28, 128) or substantially directed along filament 28, 128. Serrations, dentations or other gripping features may be found at the tip or between tip and base of some or all such barbs. As indicated in the drawings, barbs 199 may be placed along the inner concave surface 188 of seal 126 (or along surface 88 of seal 26), and formed or prepared to lay somewhat along that inner concave surface in the unstressed or pre-inserted state. As seal 26, 126 is pulled to force it toward the vessel's internal wall, as discussed above with respect to seal 26, the partial or complete inversion of seal 26, 126 causes barbs 199 to present their tips more directly to the vessel wall, so as to get better purchase in the vessel wall by the barbs. Combinations of one or more types of rings or other raised portions with one or more types or configurations of bumps, barbs or protrusions may be used in a single seal 26, 126.

Figure 20A:
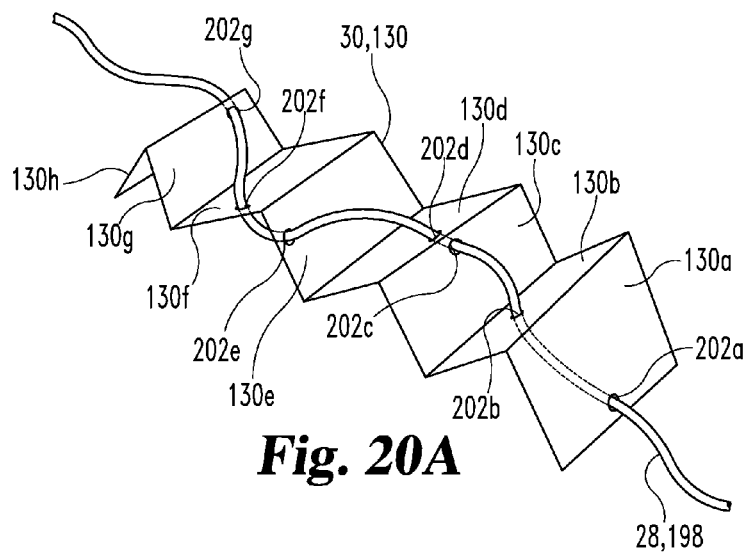
FIG. 20A-C are perspective views of embodiments of arrangements of buffer material with a filament.
Figure 20C:
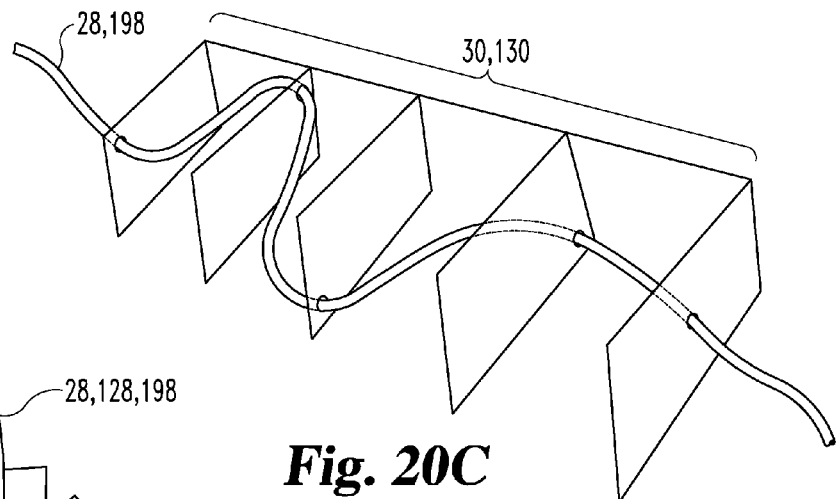
Figure 20B:
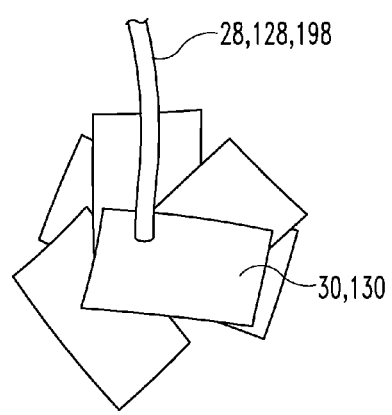

Buffer 30, 130 may be formed in a number of configurations, including those in FIGS. 20A-C which are believed to provide advantages in particular closure scenarios. In one example, buffer 30, 130 may be a sheet folded accordion-style, forming several sections or panels separated by folds, e.g. folds alternating in the direction they face. Holes through each section, such as in the geometric center of each section, accommodate filament or suture 28, 198 (e.g. one or both parts 198a, 198b of suture 198). In particular embodiments, the folded sheet is then crimped with a cylindrical crimper in order to give it a substantially cylindrical outer shape, for easier loading into a delivery device. As seal 26, 126 and buffer 30, 130 are deployed the pressure against buffer 30, 130 (e.g. by cap or disk 32, 132) tends to release the crimping, so that the folds permit buffer 30, 130 to be pressed against the vessel with its sections substantially stacked atop each other.

Other configurations beyond a simple accordion-fold with central suture holes are contemplated for buffer 30, 130. For example, as seen in FIG. 20A, an accordion-type fold may include holes in different portions of each panel or section. Section 130a has a hole 202a along one edge opposite a fold and laterally in the middle. Section 130b has a hole 202b along a fold with section 130c and laterally in the middle. Sections 130c and 130d have holes 202c, 202d along the fold between them and laterally in the middle. Sections 130e and 130f have holes 202e and 202f along one lateral edge and approximately midway between folds. Section 130g has a hole 202g in the opposite lateral edge and near a fold with section 130h. Such patterns or others may repeat in subsequent or additional sections. As seen in FIG. 20C, a similar placement of holes is shown in sections or panels of buffer 30, 130 that are physically separate from each other, and connected initially only by suture 28, 198 threaded through them.

The positioning of the holes with respect to the panels provides the opportunity for buffer 30, 130 to form a particular pattern and/or spread along the vessel when forced against the vessel in locking the closure device. That is, when the suture 28, 198 is straightened and end cap 32, 132 pushes buffer 30, 130 toward the vessel, the portions or panels of buffer 30, 130 will move toward or into an orientation with the various holes 202a-g of sections 130a-g aligned. As indicated in FIG. 20B, such movement allows the panels to cover a larger area than is possible with all of the panels stacked directly or linearly on top of each other.

Figure 21A:
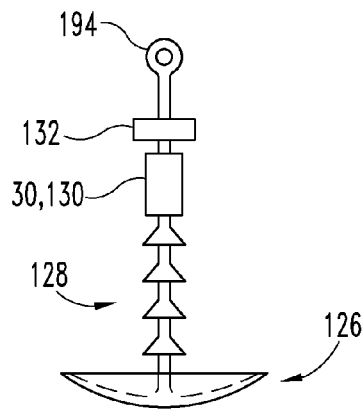
FIG. 21A-B are elevational views of the embodiment of FIG. 8A as prepared and in use.
Figure 22A:
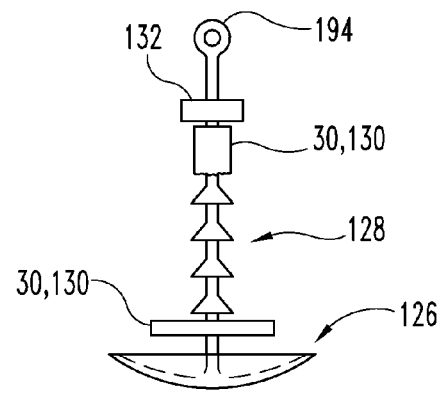
FIG. 22 A-B are elevational views of the embodiment of FIG. 8A with additional buffer material as prepared and in use.
Figure 21B:
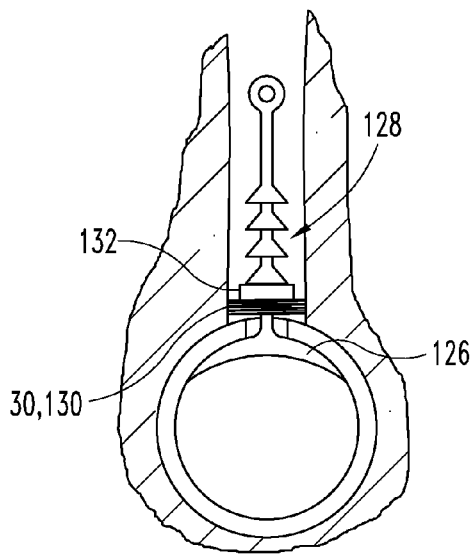
Figure 22B:
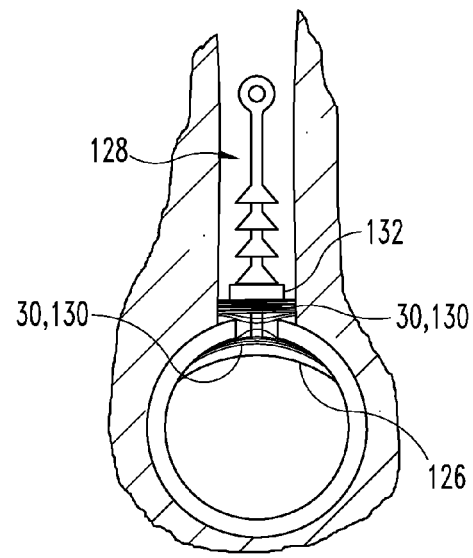

It will further be understood that a buffer 30, 130 can be loaded in different configurations or in multiple places in different embodiments, as shown in FIGS. 21A-B and 22A-B. A configuration as shown in FIG. 21A-B generally follows the description above, in which a buffer 130 is initially positioned above protrusions 192 and end cap 132 at and after loading into a delivery device (e.g. FIG. 21A). FIG. 21B indicates a configuration after insertion, with buffer 130 against the outside of a vessel or other tissue to be sealed. Another configuration (FIG. 22A) includes a second buffer 130 that is between initially protrusions 192 and seal 126, and perhaps against inner concave surface 188 of seal 126. As seal 26, 126 is inserted through the vessel wall, the second buffer 30, 130 is inserted along with it. Pulling seal 26, 126 against the inside of the vessel also presses that second buffer 30, 130 against the inside of the vessel and over at least part of the opening in the vessel. Such a second buffer may be sandwiched between the inside of the dome and the vessel wall. The first buffer 30, 130 is then forced down against the outside of the vessel wall, as indicated above (e.g. FIG. 22B). As indicated above, various types of materials may be used for buffer 30, 130, whether such a buffer is outside or inside of the vessel with which it is deployed. Tissue remodeling compositions (e.g. SIS) will naturally assist in healing of the vascular opening and/or the access opening(s) to the vessel. Other compositions that may not remodel as well as SIS, but which absorb fluid better than SIS and/or cushion the locking of the seal may reduce the likelihood of necrosis and help limit or prevent leaking from the vessel more effectively.

Thus, as indicated in description above and the drawings, embodiments of seal 126 are connected via firm and resiliently yielding stem or filament 128 and suture 198 through buffer 130, end cap 132 and pusher 200. Suture 198 extends through an introducing device (e.g. tube 24), as discussed above.

In use, the combination of seal 126 and stem or filament 128 (e.g. closure piece 129), buffer 130, end cap 132 and pusher 200 is loaded into a device for insertion as above. Placement occurs much as described above with respect to seal 26, filament 28 and buffer 30, e.g. with seal 126 inserted through an opening (e.g. in the wall of a vessel) and stem or filament 128 passing through the opening. Tension is maintained on suture 198, which tension passes through filament 128, so that seal 126 is pressed against the surface surrounding the opening (e.g. the internal wall of a vessel). Locking of seal 126 in place is by moving end cap or disk 132 over protrusions 192, as with pusher 200 to force cap 132 distally, so as to force or maintain one or more buffers 130 against the inside or outside surfaces around the opening.

When closure piece 129 is positioned and locked as desired, the user cuts one or both portions 198a, 198b of suture 198, for example at a location of suture 198 outside of the patient's skin. One of the portions 198a, 198b is pulled, which pulls suture 198 through hole 195 in closure piece 129 and out of the percutaneous opening in the patient. In this way, the suture may be easily removed from the patient rather than leaving a portion within the patient. Further, the suture may be cut at any location outside the patient and removed, rather than cut at or close to skin level. Closure piece 129 along with buffer 130 and cap 132 remain in the body to seal the opening and are resorbed over time. A dressing, closure or other treatment may be applied to the percutaneous opening to assist in healing the skin or other tissues and to reduce the likelihood of infection.

It will be understood that any of the embodiments discussed herein can be used for repair of bodily openings other than in vessels. With respect to fistulae, as noted above, the embodiments described herein or other embodiments may be used to close fistula openings and to regenerate tissue within the fistula to correct it. For example, with respect to a vesicovaginal fistula, systems or structures as disclosed above are inserted through the fistula. A seal (e.g. seal 26 or 126) is deployed as indicated above to cover an opening of the fistula, either in the bladder wall or the vaginal wall. A retainer disk (e.g. disk 33, if used) can hold the seal as a buffer (e.g. buffer 30) and locking disk (e.g. disk 32) are moved over a filament (e.g. filament 28). It will be understood that in this type of usage, instead of a locking disk like disk 32, a second seal (e.g. seal 26 or 126 or similar domed component) can be used to complete the filling and sealing of the fistula. The buffer can be compressed to the extent necessary to partially or substantially completely fill the fistula, i.e., to extend partially or fully between the walls of the vagina and bladder. The locking disk (or second seal) can cover the other opening of the fistula, engaging tissue (vaginal or bladder tissue) around that opening. With the seal and locking disk over each opening and engaging tissue, with tensioned filament connecting them and buffer at least partially filling the fistula, the fistula is treated and can heal. The descriptions of structure and methods above will be understood to be applicable to covering and sealing a variety of tissue openings necessitated by treatment or surgery or resulting from disease or trauma.

To generalize, the filament or tether with buffer or plug and seal(s) or locking disk(s) is pulled into a fistula or other opening tract by deploying through the tract so that the buffer is in the tract and positioning the seal or capping component over the opening of the fistula or other opening to provide a leak tight seal. The exposed filament or tether is placed under tension and a disk, seal or other locking component threaded over it to contact the plug. Such locking component is then pushed against the buffer to compress (accordion) the buffer into the fistula to the point of partially or completely filling the tract. The component is then locked in place by either tying the filament around it or by using beads or protrusions (as indicated above) along the filament over which the locking component could be advanced.

Embodiments of seals (e.g. seal 26) having variations in thickness as discussed previously are improvements over plain flaps. As noted above, the center portion of seal 26 is the thickest in the illustrated embodiment, with the thickness of seal 26 decreasing (e.g. substantially uniformly) out to rim 84, 84', with the exception of bead 89'. Such thinning or feathering of seal 26, along with its flexibility and invertability, provides a close fit with tissue (e.g. the inside of a blood vessel) while presenting a surface away from the tissue that does not impede flow yet is pressed into the tissue by flow. The thin rim 84, 84' of seal 26 presents little or no edge to fluid (e.g. blood, in the vascular context), and so flow is not blocked and little or no fluid can get under rim 84, 84'. The middle of external surface 86 of seal 26 is further away from the tissue than is the external surface 86 at rim 84, 84', and the pressure of flow over external surface 86 helps to keep seal 26 in place and flat against the tissue.

In embodiments in which seal 26 is pulled against the tissue so that seal 26 is at least partially deformed, the deformation provides a reactionary bias in seal 26. The bias in seal 26, in which the material of seal 26 seeks to regain its original undeformed configuration, acts to press seal 26 (particularly flattened area 84a, bead 89' and/or other parts of the interior of seal 26) against the tissue. With the middle of seal 26 pulled toward the tissue, seal 26 resists that pull, pressing seal 26 to the tissue. The opening is thus sealed by seal 26 not only because locking disk 32 acts to hold seal 26 against the tissue, but also because the deformed seal 26 reacts to the deformation by pressing itself, particularly flattened area 84a, bead 89' or another part of the inside of seal 26, against the tissue.

While other devices rely on a clot forming at the opening in the wall of the vessel, and so result in substantial oozing from the opening while a clot is forming, embodiments such as those noted above cover the inside of the opening. Closure is maintained by tension on the seal, and by deforming the seal so that a portion of it is held against the vessel by the reaction of the seal to the deformation.

As used herein, the term "filament" indicates a thin structure, such as thread 28 (e.g. items with no rigidity but which can be pulled taut) or stem 128 (e.g. items which have sufficient rigidity to extend substantially linearly by themselves, but which may have flexibility or elasticity under stress). The term "suture" is intended to mean a particular type of filament such as a strand or thread (e.g. items 28 or 198), whether or not of material(s) commonly associated with surgical sutures. It will be understood that materials other than those commonly used for surgical sutures may be used for sutures as described herein.

While the subject matter herein has been illustrated and described in detail in the exemplary drawings and foregoing description, the same is to be considered as illustrative and not restrictive in character, it being understood that only the preferred embodiment(s) have been shown and described and that all changes and modifications that come within the spirit of the disclosure are desired to be protected. It will be understood that structures, methods or other features described particularly with one embodiment can be similarly used or incorporated in or with respect to other embodiments.

What is claimed is:

1. A tissue-opening closure system, comprising:
   a seal device having a relaxed configuration with a domed shape, said seal while in said domed shape having a convex exterior surface, an opposite open concave interior surface, and a rim adjacent said convex and concave surfaces, said seal device adapted to contact a portion of tissue around a tissue-opening with at least part of the concave interior surface;
   a flexible stem fixed to said seal, said stem having a plurality of protuberances fixed thereto and a hole;
   a suture threaded through said hole and extending away from said seal device;
   a compressible buffer connected to said stem and being slidable with respect to said stem and said protuberances;
   a locking member having an opening, said locking member adapted to slide along said stem and allow said protuberances through said central opening whereafter said protuberances resist travel back through said opening, said locking member slidable along said stem so as to compress said compressible buffer, wherein the suture loops through the hole and has two free ends, said free ends extending through said buffer.

2. The system of claim 1, wherein said suture is movable with respect to said stem.

3. The system of claim 1, wherein said stem and said seal device are monolithic and made of the same bioresorbable material.

4. The system of claim 1, wherein said buffer is initially connected to said stem in a position along said suture, so that said buffer is slidable along said suture and over said stem.

5. The system of claim 4, wherein said buffer is initially in a substantially cylindrical form when positioned along said suture.

6. The system of claim 5, wherein said buffer flattens through moving along said stem and pressing against tissue.

7. The system of claim 6, wherein said suture passes through said buffer in a predetermined manner so that when said buffer flattens it assumes a desired non-cylindrical flattened form.

8. The system of claim 1, wherein said seal device is one of tear-shaped, leaf-shaped and shaped of overlapping at least part circular portions.

9. The system of claim 1, wherein said seal device includes one or more protrusions for engaging tissue extending from said concave interior surface.

10. The device of claim 1, wherein the flexible stem has a distal end that is fixed to the seal and a proximal end, the proximal end having a portion with a larger diameter than the diameter of the stem, wherein the hole extends through the larger diameter portion.

11. The device of claim 1, wherein the buffer is movable between the hole and the seal device.

12. The device of claim 1, wherein the protrusions are between the hole and the seal device.

13. A device for closing a hole in a bodily vessel, comprising:
a flexible monolithic structure including a domed seal member and a filament connected to said seal member, said seal member sized and configured for receipt against an interior surface of the vessel to cover the hole, said seal member while in a relaxed configuration having a convex exterior surface, an opposite open concave interior surface, and a rim adjacent said convex and concave surfaces,
said filament having an unstressed state in which it has a linear longitudinal axis and is yieldingly resilient, said filament extending away from said open concave interior surface without application of force to said filament, said filament having frustoconical protrusions along it and an end portion having a hole that is non-parallel to the longitudinal axis of said filament,
and wherein said domed seal member is elastically deformable under tension applied through said filament to partially or completely flatten said domed seal member whereupon at least part of the interior surface of the seal member is forced against the interior surface of the vessel.

14. The device of claim 13, wherein said monolithic structure is formed of biodegradable materials from the group consisting of polyglycolic acid polymer, polycaprolactone and mixtures thereof.

15. The device of claim 13, further comprising a suture extending through said hole of said end portion.

16. The device of claim 15, wherein said suture is looped through said hole.

17. The device of claim 15, further comprising a buffer of biodegradeable material operatively connected to said filament to be moved along said filament toward said seal member.

18. The device of claim 17, wherein said buffer is formed in folds.

19. The device of claim 18, wherein said buffer includes a number of sections separated by folds, and said suture extends through a plurality of said sections, and wherein the point at which said suture goes through each of said plurality of sections varies from section to section.

20. The device of claim 19, wherein said buffer sections only partially overlap each other in use so that said sections span an area larger than the area of any particular section.

21. The device of claim 13, wherein said inner concave surface of said seal member includes at least one protrusion raised above said inner concave surface and positioned laterally to said filament.

22. The device of claim 21, wherein said at least one protrusion includes at least one bead forming a ring around said filament.

23. The device of claim 21, wherein said at least one protrusion includes a plurality of barbs.

24. The device of claim 21, wherein said protrusions are monolithic with and made of the same material as said seal member.

25. A tissue-opening closure system, comprising:
an internal member having a relaxed configuration with a domed shape, said internal member while in said domed shape having a convex exterior surface, an opposite open concave interior surface, and a rim adjacent said convex and concave surfaces, said internal member adapted to contact a portion of tissue around a tissue-opening with at least part of the concave interior surface;
a flexible stem fixed to said internal member, said stem having a plurality of protuberances fixed thereto and a hole;
a suture threaded through said hole and extending away from said internal member, wherein the suture loops through the hole and has two free ends, said free ends extending through said buffer;
a first compressible buffer connected to said stem and being slidable with respect to said stem and said protuberances;
a second buffer connected to said stem between said protuberances and said internal member; and
a locking member having an opening, said locking member adapted to slide along said stem and allow said protuberances through said central opening whereafter said protuberances resist travel back through said opening, said locking member slidable along said stem so as to compress said first compressible buffer.

26. A tissue-opening closure system, comprising:
an internal member having a relaxed configuration with a domed shape, said internal member while in said domed shape having a convex exterior surface, an opposite open concave interior surface, and a rim adjacent said convex and concave surfaces, said internal member adapted to contact a portion of tissue around a tissue-opening with at least part of the concave interior surface;
a flexible stem fixed to said internal member, said stem having a plurality of protuberances fixed thereto and a hole, said stem having an end portion having a hole that is non-parallel to the longitudinal axis of said stem;
a suture threaded through said hole and extending away from said internal member;
a first compressible buffer connected to said stem and being slidable with respect to said stem and said protuberances;
a second buffer connected to said stem between said protuberances and said internal member; and
a locking member having an opening, said locking member adapted to slide along said stem and allow said protuberances through said central opening whereafter said protuberances resist travel back through said opening, said locking member slidable along said stem so as to compress said first compressible buffer.

* * * * *

UNITED STATES PATENT AND TRADEMARK OFFICE
CERTIFICATE OF CORRECTION

| | |
|---|---|
| PATENT NO. | : 8,932,325 B2 |
| APPLICATION NO. | : 13/303707 |
| DATED | : January 13, 2015 |
| INVENTOR(S) | : Cleon Stanley |

It is certified that error appears in the above-identified patent and that said Letters Patent is hereby corrected as shown below:

In the Claims
Col. 24, claim 25, line 33, insert --first compressible-- after "said" and before "buffer".

Signed and Sealed this
Twenty-ninth Day of September, 2015

Michelle K. Lee
*Director of the United States Patent and Trademark Office*